(12) United States Patent
Harada et al.

(10) Patent No.: US 7,862,980 B2
(45) Date of Patent: Jan. 4, 2011

(54) SALT SUITABLE FOR AN ACID GENERATOR AND A CHEMICALLY AMPLIFIED POSITIVE RESIST COMPOSITION CONTAINING THE SAME

(75) Inventors: Yukako Harada, Settsu (JP); Isao Yoshida, Ikeda (JP); Yoshiyuki Takata, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 361 days.

(21) Appl. No.: 11/882,084

(22) Filed: Jul. 30, 2007

(65) Prior Publication Data
US 2008/0081293 A1   Apr. 3, 2008

(30) Foreign Application Priority Data
Aug. 2, 2006 (JP) ............... 2006-210688

(51) Int. Cl.
G03F 7/004 (2006.01)
C07C 309/12 (2006.01)
C07D 307/30 (2006.01)

(52) U.S. Cl. .............. 430/270.1; 430/921; 430/922; 560/126; 562/109; 562/113

(58) Field of Classification Search ............. 430/270.1, 430/921, 922; 560/126; 562/109, 113
See application file for complete search history.

(56) References Cited

U.S. PATENT DOCUMENTS

| | | | |
|---|---|---|---|
| 6,348,297 B1 | 2/2002 | Uetani et al. | |
| 6,383,713 B1 | 5/2002 | Uetani et al. | |
| 6,548,220 B2 | 4/2003 | Uetani et al. | |
| 6,548,221 B2 | 4/2003 | Uetani et al. | |
| 6,824,957 B2 | 11/2004 | Okino et al. | |
| 6,893,792 B2 | 5/2005 | Miya et al. | |
| 6,908,722 B2 | 6/2005 | Ebata et al. | |
| 7,262,321 B2 | 8/2007 | Harada et al. | |
| 7,301,047 B2 * | 11/2007 | Yoshida et al. | 560/129 |
| 7,304,175 B2 | 12/2007 | Harada et al. | |
| 2003/0194639 A1 | 10/2003 | Miya et al. | |
| 2006/0019042 A1 | 1/2006 | Nojima et al. | |
| 2006/0194982 A1 | 8/2006 | Harada et al. | |
| 2007/0027336 A1 * | 2/2007 | Yoshida et al. | 560/129 |
| 2007/0078269 A1 * | 4/2007 | Harada et al. | 549/266 |
| 2007/0100096 A1 | 5/2007 | Harada et al. | |
| 2007/0100158 A1 | 5/2007 | Harada et al. | |
| 2007/0100159 A1 | 5/2007 | Yoshida et al. | |
| 2007/0122750 A1 | 5/2007 | Yamaguchi et al. | |
| 2007/0148702 A1 | 6/2007 | Nakamura et al. | |
| 2007/0184382 A1 | 8/2007 | Yamaguchi et al. | |
| 2008/0086014 A1 * | 4/2008 | Shigematsu et al. | 558/52 |
| 2008/0166660 A1 * | 7/2008 | Takata et al. | 430/281.1 |
| 2008/0193874 A1 | 8/2008 | Takata et al. | |
| 2008/0213695 A1 * | 9/2008 | Yamaguchi et al. | 430/281.1 |

FOREIGN PATENT DOCUMENTS

| | | |
|---|---|---|
| EP | 1041442 A1 | 10/2000 |
| EP | 1077391 A1 | 2/2001 |
| EP | 1167349 A1 | 1/2002 |
| GB | 2441032 A | 2/2008 |
| JP | 2002-202607 A | 7/2002 |
| JP | 2002-265436 A | 9/2002 |
| JP | 2003-122012 A | 4/2003 |
| JP | 2003-131383 A | 5/2003 |
| JP | 2004-4561 A | 1/2004 |
| JP | 2004-117959 A | 4/2004 |
| JP | 2006-306856 A | 11/2006 |

* cited by examiner

*Primary Examiner*—John S Chu
(74) *Attorney, Agent, or Firm*—Birch, Stewart, Kolasch & Birch, LLP

(57) ABSTRACT

The present invention provides a salt represented by the formula (I):

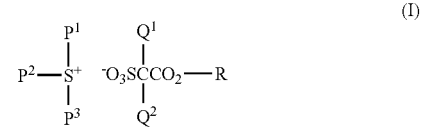

wherein $P^1$, $P^2$, $P^3$, $Q^1$, $Q^2$ and R are defined in the specification and the present invention further provides a chemically amplified resist composition comprising the salt represented by the above-mentioned formula (I).

21 Claims, No Drawings

SALT SUITABLE FOR AN ACID GENERATOR AND A CHEMICALLY AMPLIFIED POSITIVE RESIST COMPOSITION CONTAINING THE SAME

This nonprovisional application claims priority under 35 U.S.C. §119(a) on Patent Application No. 2006-210688 filed in JAPAN on Aug. 2, 2006, the entire contents of which are hereby incorporated by reference.

FIELD OF THE INVENTION

The present invention relates to a salt suitable for an acid generator used for a chemically amplified resist composition which is used in fine processing of semiconductors, and a chemically amplified positive resist composition containing the same.

BACKGROUND OF THE INVENTION

A chemically amplified positive resist composition used for semiconductor microfabrication employing a lithography process contains an acid generator comprising a compound generating an acid by irradiation.

In semiconductor microfabrication, it is desirable to form patterns having high resolution and high sensitivity, and it is expected for a chemically amplified resist composition to give such patterns.

U.S. Pat. No. 6,548,221 B2 and U.S. Pat. No. 6,383,713 B1 disclose a chemically amplified resist composition containing triphenylsulfonium perfluorobutanesulfonate as the acid generator.

US 2003/0194639 A1 also discloses a chemically amplified resist composition containing the salt represented by the following formulae:

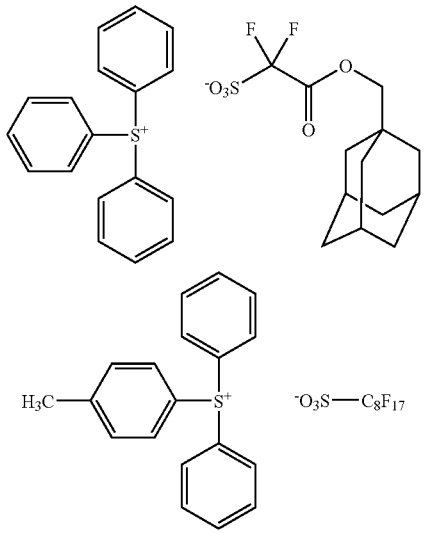

or the like as the acid generator.

SUMMARY OF THE INVENTION

An object of the present invention is to provide a salt suitable for an acid generator capable of providing chemically amplified resist compositions giving patterns having higher sensitivity and high resolution.

Other object of the present invention is to provide a chemically amplified resist composition containing the salt.

These and other objects of the present invention will be apparent from the following description.

The present invention relates to the followings:

<1> A salt represented by the formula (I):

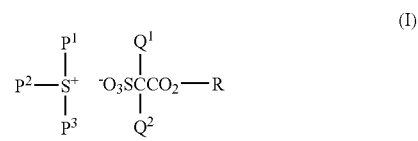

wherein $P^1$, $P^2$ and $P^3$ each independently represent a C1-C30 alkyl group which may be substituted with at least one selected from a hydroxyl group, a C3-C12 cyclic hydrocarbon group and a C1-C12 alkoxy group, or a C3-C30 cyclic hydrocarbon group which may be substituted with at least one selected from a hydroxyl group and a C1-C12 alkoxy group, provided that all of $P^1$, $P^2$ and $P^3$ are not simultaneously phenyl groups which may be substituted, $Q^1$ and $Q^2$ each independently represent a fluorine atom or a C1-C6 perfluoroalkyl group, and R represents a group represented by the formula:

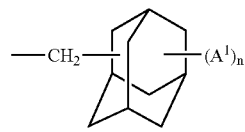

wherein $A^1$ represents —OH or —$Y^1$—OH, n represents an integer of 1 to 9, and $Y^1$ represents a divalent C1-C6 saturated aliphatic hydrocarbon group;

a group represented by the formula:

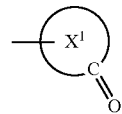

wherein ring $X^1$ represents a C3-C30 monocyclic or polycyclic hydrocarbon group in which one —$CH_2$— group is substituted with —CO—, and at least one hydrogen atom in the monocyclic or polycyclic hydrocarbon group may be substituted with a C1-C6 alkyl group, a C1-C6 alkoxy group, a C1-C4 perfluoroalkyl group, a C1-C6 hydroxyalkyl group, a hydroxyl group or a cyano group;

a group represented by the formula:

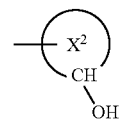

wherein ring $X^2$ represents a C3-C30 monocyclic or polycyclic hydrocarbon group in which a hydrogen atom of one —$CH_2$— group is substituted with a hydroxyl group, and at least one hydrogen atom in the monocyclic or polycyclic hydrocarbon group may be substituted with a C1-C6 alkyl group, a C1-C6 alkoxy group, a C1-C4 perfluoroalkyl group, a C1-C6 hydroxyalkyl group, a hydroxyl group or a cyano group;

a group represented by the formula:

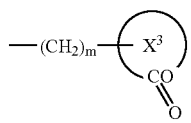

wherein ring $X^3$ represents a C3-C30 monocyclic or polycyclic hydrocarbon group in which one —$CH_2$— group is substituted with —COO—, and at least one hydrogen atom in the monocyclic or polycyclic hydrocarbon group may be substituted with a C1-C6 alkyl group, a C1-C6 alkoxy group, a C1-C4 perfluoroalkyl group, a C1-C6 hydroxyalkyl group, a hydroxyl group or a cyano group, and m represents an integer of 0 to 12; or a group represented by the formula:

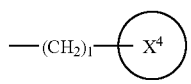

wherein ring $X^4$ represents a C6-C30 polycyclic hydrocarbon group having tricycle or more, and at least one hydrogen atom in the polycyclic hydrocarbon group may be substituted with a C1-C6 alkyl group, a C1-C6 alkoxy group, a C1-C4 perfluoroalkyl group, a C1-C6 hydroxyalkyl group or a cyano group, and l represents an integer of 1 to 12;

<2> The salt according to <1>, wherein $Q^1$ and $Q^2$ each independently represent a fluorine atom or a trifluoromethyl group;

<3> The salt according to <1> or <2>, wherein the salt is one represented by the formula (Ia):

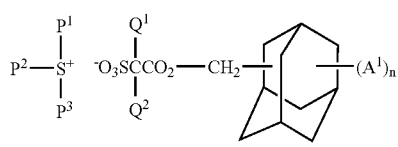

wherein $P^1$, $P^2$, $P^3$, $Q^1$, $Q^2$, $A^1$ and n have the same meanings as defined above;

<4> The salt according to <3>, wherein $A^1$ is —OH or —$CH_2OH$, and n is 1 or 2;

<5> The salt according to <1> or <2>, wherein the salt is one represented by the formula (Ib):

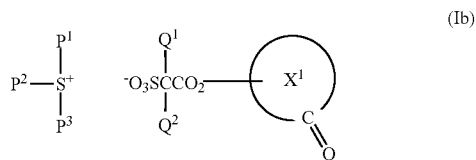

wherein $P^1$, $P^2$, $P^3$, $Q^1$, $Q^2$, and $X^1$ have the same meanings as defined above;

<6> The salt according to <5>, wherein ring $X^1$ is a C4-C8 oxocycloalkyl group, an oxoadamantyl group or an oxonorbornyl group, and at least one hydrogen atom in each of the groups may be substituted with a C1-C6 alkyl group, a C1-C6 alkoxy group, a C1-C4 perfluoroalkyl group, a C1-C6 hydroxyalkyl group, a hydroxyl group or a cyano group;

<7> The salt according to <1> or <2>, wherein the salt is one represented by the formula (Ic):

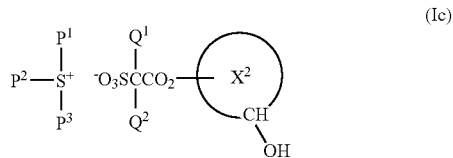

wherein $P^1$, $P^2$, $P^3$, $Q^1$, $Q^2$, and $X^2$ have the same meanings as defined above;

<8> The salt according to <7>, wherein ring $X^2$ is a C4-C8 hydroxycycloalkyl group, a hydroxyadamantyl group or a hydroxynorbornyl group, and at least one hydrogen atom in each of the groups may be substituted with a C1-C6 alkyl group, a C1-C6 alkoxy group, a C1-C4 perfluoroalkyl group, a C1-C6 hydroxyalkyl group, a hydroxyl group or a cyano group;

<9> The salt according to <1> or <2>, wherein the salt is one represented by the formula (Id):

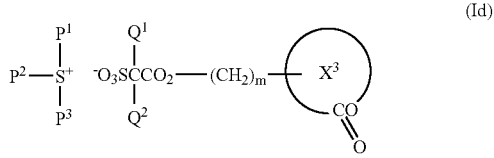

wherein $P^1$, $P^2$, $P^3$, $Q^1$, $Q^2$, $X^3$ and m have the same meanings as defined above;

<10> The salt according to <9>, wherein ring $X^3$ is a monovalent residue of a compound represented by the formula (IIa), (IIb) or (IIc):

-continued

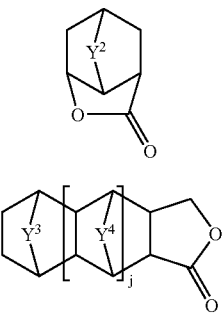
(IIb)

(IIc)

wherein $Y^2$, $Y^3$ and $Y^4$ each independently represent (a) an alkylene group or (b) no bonding and a hydrogen atom in each side, k represents an integer of 1 to 4, j represents an integer of 0 to 2, and at least one hydrogen atom in the formulae (IIIa), (IIIb) and (IIIc) may be substituted with a C1-C6 alkyl group, a C1-C6 alkoxy group, a C1-C4 perfluoroalkyl group, a C1-C6 hydroxyalkyl group, a hydroxyl group or a cyano group;

<11> The salt according to <1> or <2>, wherein the salt is one represented by the formula (Ie):

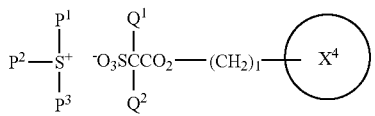
(Ie)

wherein $P^1$, $P^2$, $P^3$, $Q^1$, $Q^2$, $X^4$ and l have the same meanings as defined above;

<12> The salt according to <11>, wherein ring $X^4$ is a monovalent residue of a compound represented by the formula (IIIa) or (IIIb):

(IIIa)

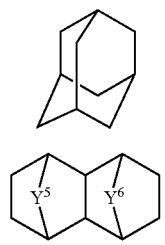

(IIIb)

wherein $Y^5$ represents (a) an alkylene group or (b) an oxygen atom, and $Y^6$ represents (a) an alkylene group, (b) an oxygen atom or (c) no bonding and hydrogen atom in each side, and at least one hydrogen atom in the formulae (IIIa) and (IIIb) may be substituted with a C1-C6 alkyl group, a C1-C6 alkoxy group, a C1-C4 perfluoroalkyl group or a cyano group.

<13> The salt according to any one of <1> to <12>, wherein at least two selected from $P^1$, $P^2$ and $P^3$ are independently aryl groups which may be substituted with at least one selected from a hydroxyl group and a C1-C12 alkoxy group;

<14> The salt according to <3>, wherein the salt represented by the formula (Ia) is one represented by the formula (IVa), (IVb), (IVc) or (IVd);

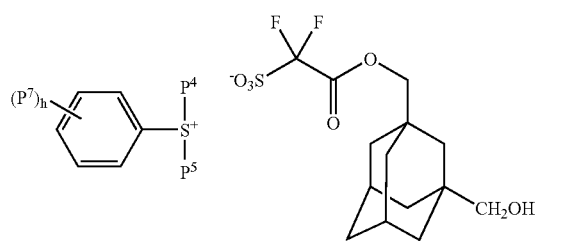
(IVa)

(IVb)

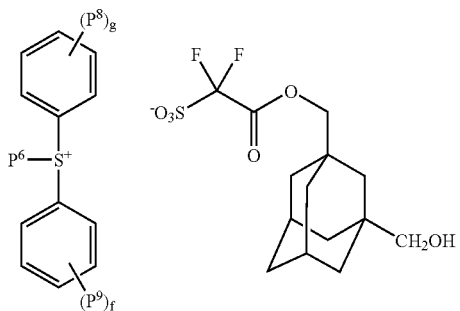
(IVc)

(IVd)

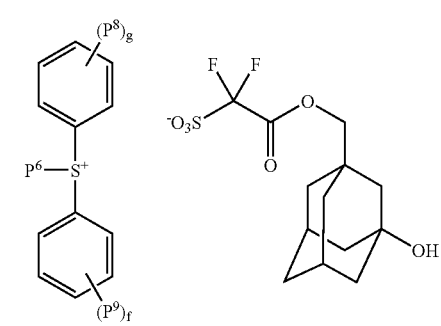

wherein $P^4$ and $P^5$ each independently represent a C1-C20 alkyl group which may be substituted with at least one selected from a hydroxyl group, a C3-C12 cyclic hydrocarbon group and a C1-C12 alkoxy group, or a C3-C30 cyclic hydrocarbon group which may be substituted with at least one selected from a hydroxyl group and a C1-C12 alkoxy group, provided that all of $P^4$ and $P^5$ are not simultaneously phenyl groups which may be substituted, $P^6$ represents a C1-C20 alkyl group which may be substituted with at least one selected from a hydroxyl group, a C3-C12 cyclic hydrocarbon group and a C1-C12 alkoxy group, or a C3-C30 cyclic hydrocarbon group which may be substituted with at least one selected from a hydroxyl group and a C1-C12 alkoxy group, provided that $P^6$ is not a phenyl group which may be substituted, $P^7$, $P^8$ and $P^9$ each independently represent a hydroxyl group, a C1-C12 alkyl group, a C1-C12 alkoxy group or a C3-C12 cyclic hydrocarbon group, and f, g and h each independently represent an integer of 0 to 5;

<15> The salt according to <5>, wherein the salt represented by the formula (Ib) is one represented by the formula (IVe) or (IVf);

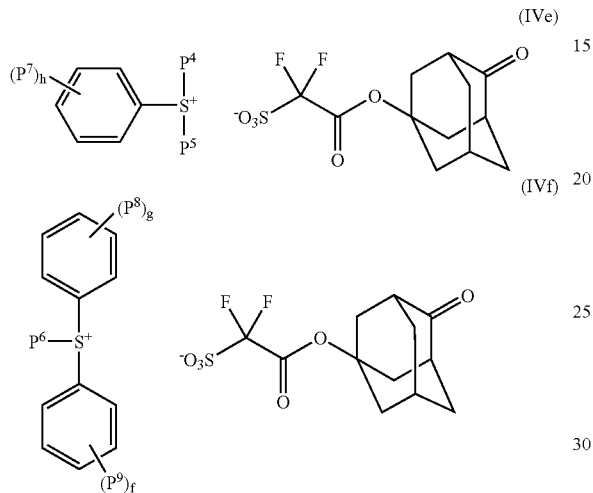

wherein $P^4$, $P^5$, $P^6$, $P^7$, $P^8$, $P^9$, f, g and h have the same meanings as defined above;

<16> The salt according to <7>, wherein the salt represented by the formula (Ic) is one represented by the formula (IVg) or (IVh);

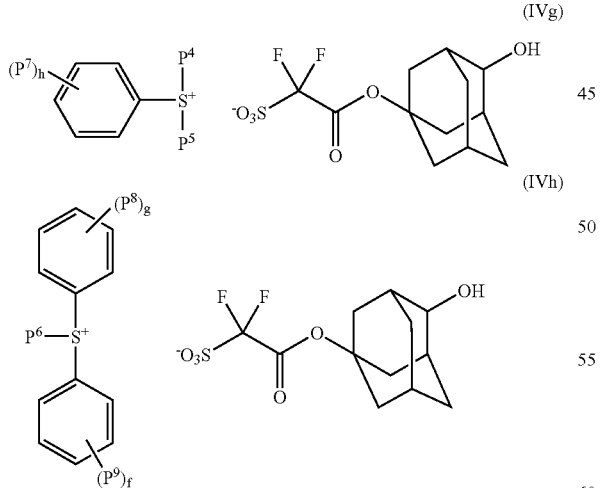

wherein $P^4$, $P^5$, $P^6$, $P^7$, $P^8$, $P^9$, f, g and h have the same meanings as defined above;

<17> The salt according to <9>, wherein the salt represented by the formula (Id) is one represented by the formula (IVi), (IVj), (IVk) or (IVl):

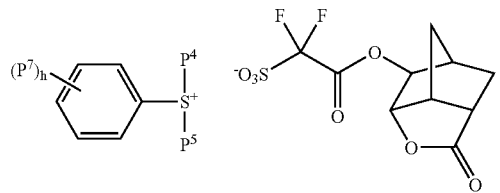

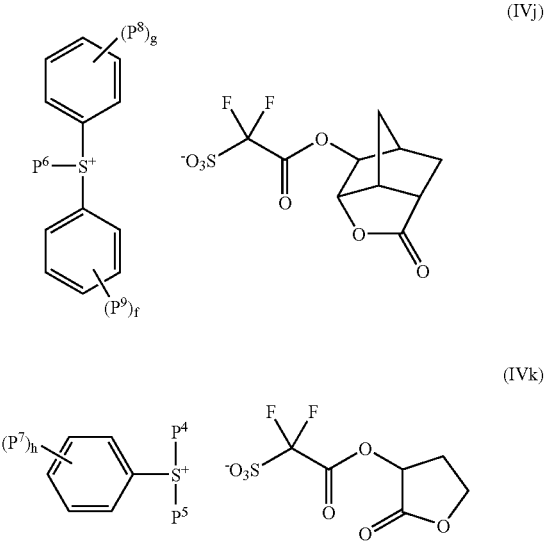

wherein $P^4$, $P^5$, $P^6$, $P^7$, $P^8$, $P^9$, f, g and h have the same meanings as defined above;

<18> The salt according to <11>, wherein the salt represented by the formula (Ie) is one represented by the formula (IVm) or (IVn):

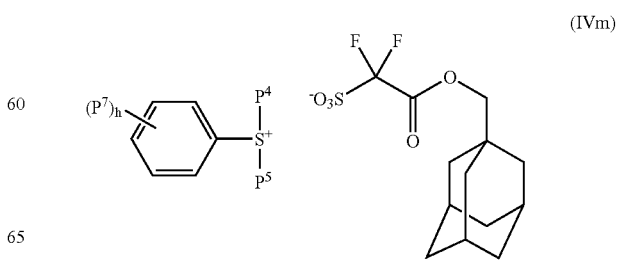

-continued

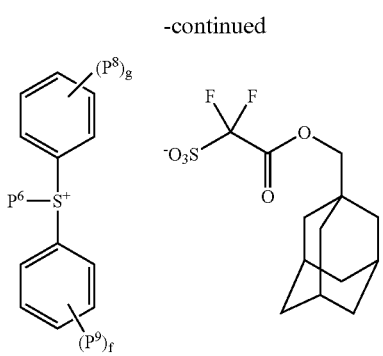

wherein $P^4$, $P^5$, $P^6$, $P^7$, $P^8$, $P^9$, f, g and h have the same meanings as defined above;

<19> A chemically amplified positive resist composition comprising a salt represented by the formula (I):

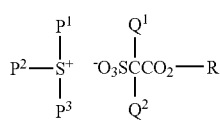

wherein $P^1$, $P^2$ and $P^3$ each independently represent a C1-C30 alkyl group which may be substituted with at least one selected from a hydroxyl group, a C3-C12 cyclic hydrocarbon group and a C1-C12 alkoxy group, or a C3-C30 cyclic hydrocarbon group which may be substituted with at least one selected from a hydroxyl group and a C1-C12 alkoxy group, provided that all of $P^1$, $P^2$ and $P^3$ are not simultaneously phenyl groups which may be substituted, $Q^1$ and $Q^2$ each independently represent a fluorine atom or a C1-C6 perfluoroalkyl group, and R represents
a group represented by the formula:

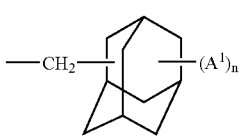

wherein $A^1$ represents —OH or —$Y^1$—OH, n represents an integer of 1 to 9, and $Y^1$ represents a divalent C1-C6 saturated aliphatic hydrocarbon group;
a group represented by the formula:

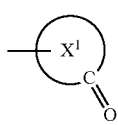

wherein ring $X^1$ represents a C3-C30 monocyclic or polycyclic hydrocarbon group in which one —$CH_2$— group is substituted with —CO—, and at least one hydrogen atom in the monocyclic or polycyclic hydrocarbon group may be substituted with a C1-C6 alkyl group, a C1-C6 alkoxy group, a C1-C4 perfluoroalkyl group, a C1-C6 hydroxyalkyl group, a hydroxyl group or a cyano group;
a group represented by the formula:

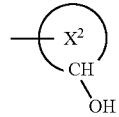

wherein ring $X^2$ represents a C3-C30 monocyclic or polycyclic hydrocarbon group in which a hydrogen atom of one —$CH_2$— group is substituted with a hydroxyl group, and at least one hydrogen atom in the monocyclic or polycyclic hydrocarbon group may be substituted with a C1-C6 alkyl group, a C1-C6 alkoxy group, a C1-C4 perfluoroalkyl group, a C1-C6 hydroxyalkyl group, a hydroxyl group or a cyano group;
a group represented by the formula:

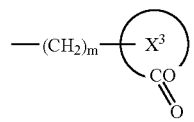

wherein ring $X^3$ represents a C3-C30 monocyclic or polycyclic hydrocarbon group in which one —$CH_2$— group is substituted with —COO—, and at least one hydrogen atom in the monocyclic or polycyclic hydrocarbon group may be substituted with a C1-C6 alkyl group, a C1-C6 alkoxy group, a C1-C4 perfluoroalkyl group, a C1-C6 hydroxyalkyl group, a hydroxyl group or a cyano group, and m represents an integer of 0 to 12; or
a group represented by the formula:

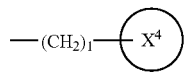

wherein ring $X^4$ represents a C6-C30 polycyclic hydrocarbon group having tricycle or more, and at least one hydrogen atom in the polycyclic hydrocarbon group may be substituted with a C1-C6 alkyl group, a C1-C6 alkoxy group, a C1-C4 perfluoroalkyl group, a C1-C6 hydroxyalkyl group or a cyano group, and l represents an integer of 1 to 12, and a resin which contains a structural unit which has an acid-labile group and which itself is insoluble or poorly soluble in an aqueous alkali solution but becomes soluble in an aqueous alkali solution by the action of an acid;

<20> The chemically amplified positive resist composition according to <19>, wherein $Q^1$ and $Q^2$ each independently represent a fluorine atom or a trifluoromethyl group;

<21> The chemically amplified positive resist composition according to <19> or <20>, wherein the resin contains a structural unit derived from a monomer having a bulky and acid-labile group;

<22> The chemically amplified positive resist composition according to <21>, wherein the bulky and acid-labile group is a 2-alkyl-2-adamantyl ester group or a 1-(1-adamantyl)-1-alkylalkyl ester group;

<23> The chemically amplified positive resist composition according to <21>, wherein the monomer having a bulky and acid-labile group is 2-alkyl-2-adamantyl acrylate, 2-alkyl-2-adamantyl methacrylate, 1-(1-adamantyl)-1-alkylalkyl acrylate, 1-(1-adamantyl)-1-alkylalkyl methacrylate, 2-alkyl-2-adamantyl 5-norbornene-2-carboxylate, 1-(1-adamantyl)-1-alkylalkyl 5-norbornene-2-carboxylate, 2-alkyl-2-adamantyl α-chloroacrylate or 1-(1-adamantyl)-1-alkylalkyl α-chloroacrylate;

<24> The chemically amplified positive resist composition according to any one of <19> to <23>, wherein the chemically amplified positive resist composition further comprises a basic compound.

DESCRIPTION OF PREFERRED EMBODIMENTS

First, the present salt represented by the formula (I) (hereinafter, simply referred to as Salt (I)) will be illustrated.

In the cation part of Salt (I), $P^1$, $P^2$ and $P^3$ each independently represent a C1-C30 alkyl group which may be substituted with at least one selected from a hydroxyl group, a C3-C12 cyclic hydrocarbon group and a C1-C12 alkoxy group, or a C3-C30 cyclic hydrocarbon group which may be substituted with at least one selected from a hydroxyl group and a C1-C12 alkoxy group, provided that all of $P^1$, $P^2$ and $P^3$ are not simultaneously phenyl groups which may be substituted.

Examples of the C1-C30 alkyl group include a methyl, ethyl, propyl, isopropyl, n-butyl, isobutyl, sec-butyl, tert-butyl, n-pentyl, n-hexyl, n-octyl and 2-ethylhexyl group. Among them, the C1-C20 alkyl group is preferable and the C1-C6 alkyl group is more preferable. Examples of the C3-C12 cyclic hydrocarbon group include a cyclopentyl, cyclohexyl, adamantyl, dimethyladamantyl, phenyl, 4-methylphenyl, 4-tert-butylphenyl, 4-n-hexylphenyl and 4-phenylphenyl group, and the C5-C12 cyclic hydrocarbon group is preferable. Examples of the C1-C12 alkoxy group include a methoxy, ethoxy, n-propoxy, isopropoxy, n-butoxy, isobutoxy, sec-butoxy, tert-butoxy, n-pentyloxy, n-hexyloxy, n-octyloxy and 2-ethylhexyloxy group, and the C1-C6 alkoxy group is preferable.

Examples of the C1-C30 alkyl group substituted with at least one selected from the hydroxyl group, the C3-C12 cyclic hydrocarbon group and the C1-C12 alkoxy group include a cyclohexylmethyl, benzyl and 4-methoxybenzyl group.

Examples of the C3-C30 cyclic hydrocarbon group include a cyclopentyl, cyclohexyl, 1-adamantyl, 2-adamantyl, dimethyladamantyl, bicyclohexyl, phenyl, 2-methylphenyl, 4-methylphenyl, 4-ethylphenyl, 4-isopropylphenyl, 4-tert-butylphenyl, 2,4-dimethylphenyl, 2,4,6-trimethylphenyl, 4-n-hexylphenyl, 4-n-octylphenyl, 1-naphthyl, 2-naphthyl, fluorenyl and 4-phenylphenyl group, and the C5-C12 cyclic hydrocarbon group is preferable.

Examples of the C3-C30 cyclic hydrocarbon group substituted with at least one selected from the hydroxyl group and the C1-C12 alkoxy group include a 4-hydroxyphenyl, 4-methoxyphenyl and 4-n-hexyloxyphenyl group.

All of $P^1$, $P^2$ and $P^3$ are not simultaneously phenyl groups which may be substituted.

It is preferred that at least two selected from $P^1$, $P^2$ and $P^3$ are independently aryl groups which may be substituted with at least one selected from the hydroxyl group and the C1-C12 alkoxy group such as a phenyl, 4-methylphenyl, 4-hydroxyphenyl, 4-methoxylphenyl, 4-tert-butylphenyl, 4-n-hexylphenyl and 4-n-hexyloxyphenyl group. It is more preferred that at least two selected from $P^1$, $P^2$ and $P^3$ are independently phenyl groups which may be substituted with at least one selected from the hydroxyl group, the C1-C6 alkyl group, the C1-C6 alkoxy group and the C3-C12 cyclic hydrocarbon group.

Among them, the preferred cation parts of Salt (I) are followings.

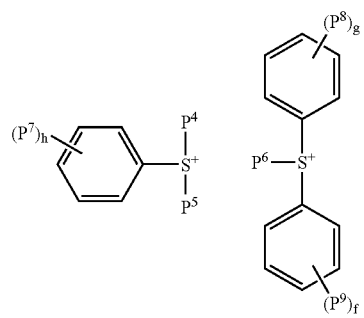

$P^4$ and $P^5$ each independently represent a C1-C20 alkyl group which may be substituted with at least one selected from a hydroxyl group, a C3-C12 cyclic hydrocarbon group and a C1-C12 alkoxy group, or a C3-C30 cyclic hydrocarbon group which may be substituted with at least one selected from a hydroxyl group and a C1-C12 alkoxy group, provided that all of $P^4$ and $P^5$ are not simultaneously phenyl groups which may be substituted.

It is preferred that $P^4$ and $P^5$ each independently represent a C1-C6 alkyl group which may be substituted with a C5-C12 cyclic hydrocarbon group, or a C5-C12 cyclic hydrocarbon group, provided that all of $P^4$ and $P^5$ are not simultaneously phenyl groups which may be substituted.

$P^6$ represents a C1-C20 alkyl group which may be substituted with at least one selected from a hydroxyl group, a C3-C12 cyclic hydrocarbon group and a C1-C12 alkoxy group, or a C3-C30 cyclic hydrocarbon group which may be substituted with at least one selected from a hydroxyl group and a C1-C12 alkoxy group, provided that $P^6$ is not a phenyl group which may be substituted.

It is preferred that $P^6$ represents a C1-C6 alkyl group which may be substituted with at least one selected from a hydroxyl group, a C5-C12 cyclic hydrocarbon group and a C1-C6 alkoxy group, or a C5-C12 cyclic hydrocarbon group which may be substituted with at least one selected from a hydroxyl group, a C5-C12 cyclic hydrocarbon group and a C1-C6 alkoxy group.

$P^7$, $P^8$ and $P^9$ each independently represent a hydroxyl group, a C1-C12 alkyl group, a C1-C12 alkoxy group or a C3-C12 cyclic hydrocarbon group, and preferably represents a hydroxyl group, a C1-C6 alkyl group, a C1-C6 alkoxy group or a C5-C12 cyclic hydrocarbon group, and f, g and h each independently represent an integer of 0 to 5, preferably an integer of 0 to 2, and more preferably 0 or 1.

Specific examples of the cation part of Salt (I) include the followings.
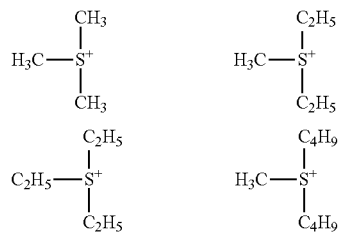
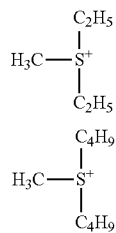
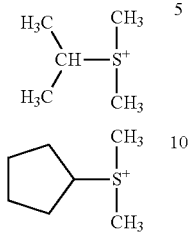
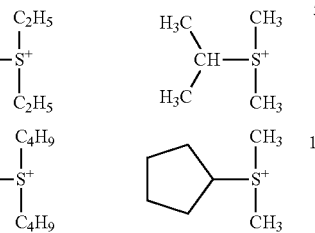
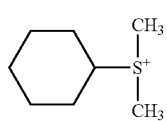
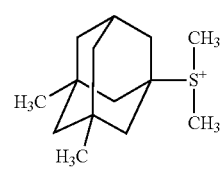
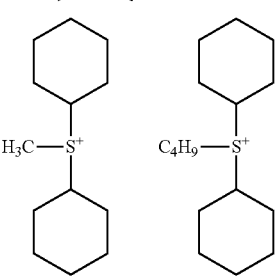
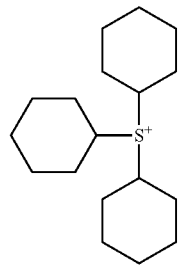
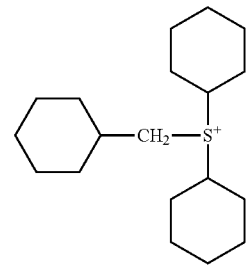
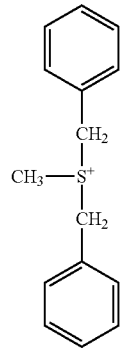
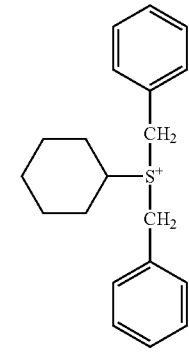
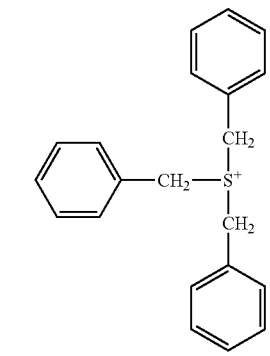
-continued
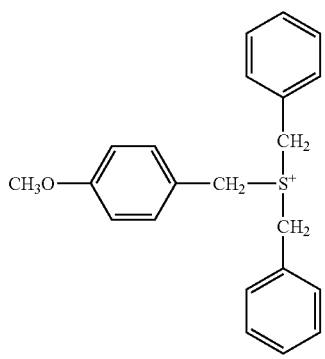
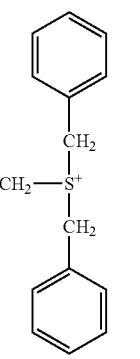
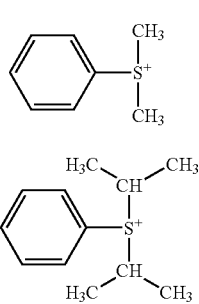
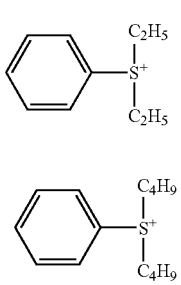
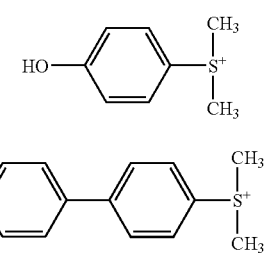
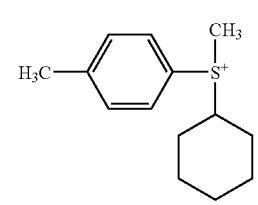
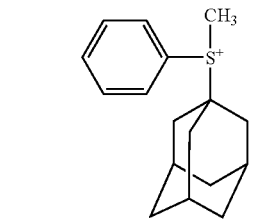
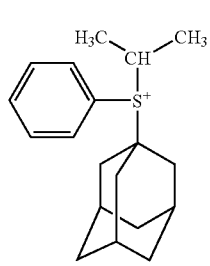
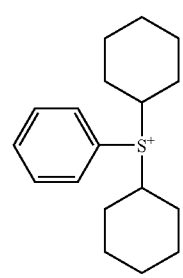

-continued
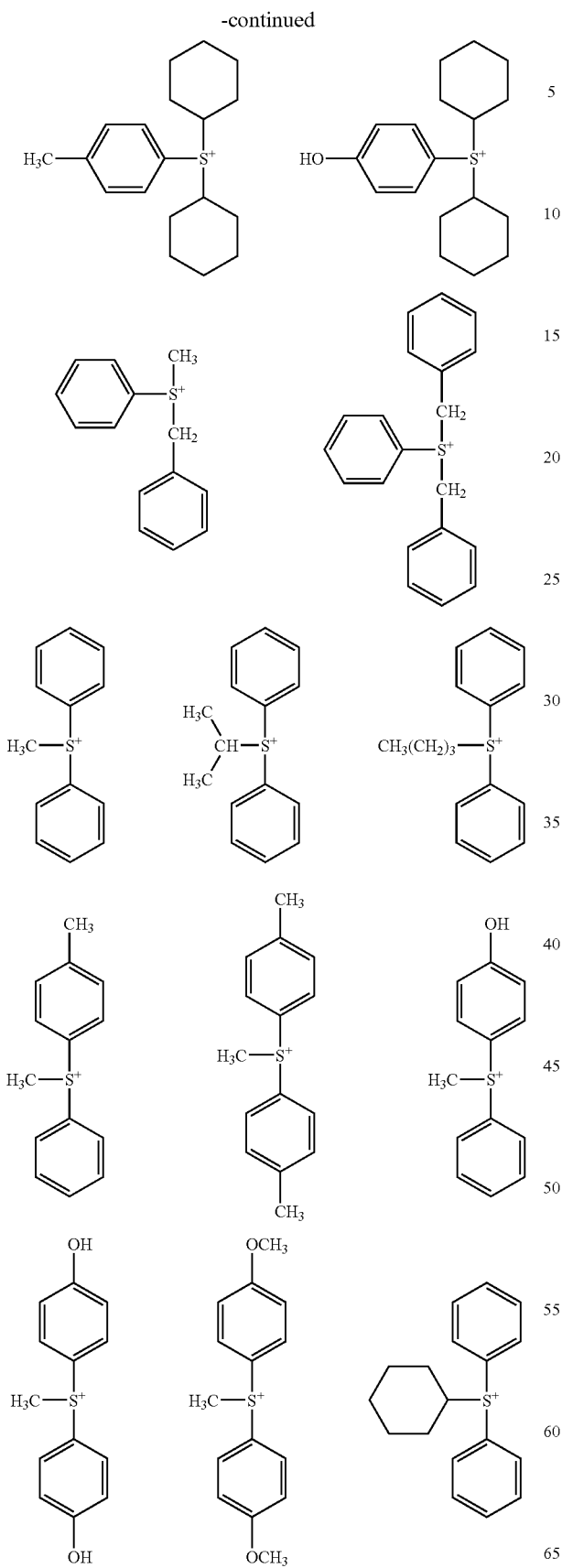
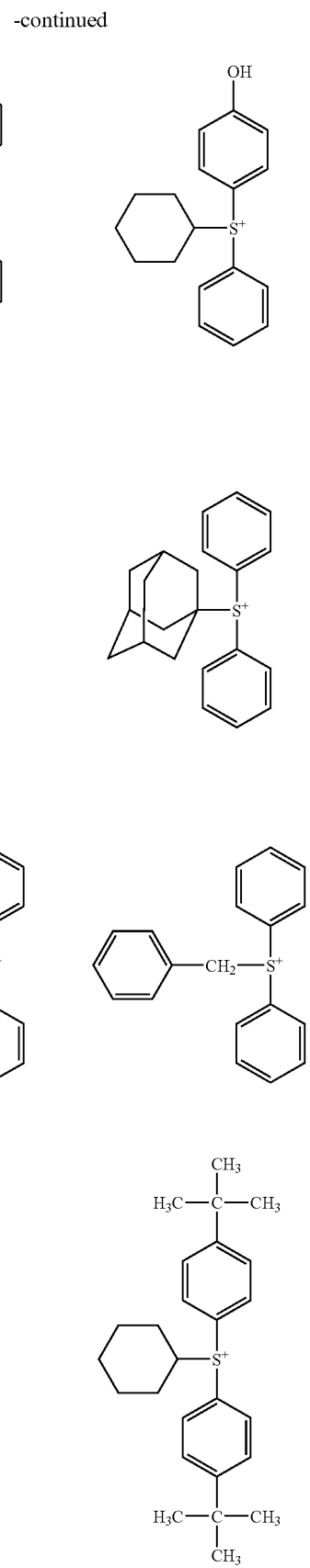

-continued

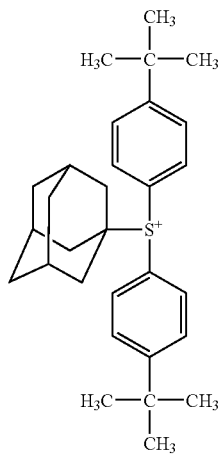

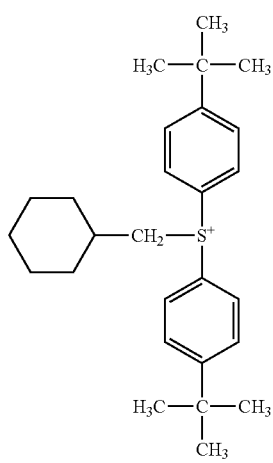

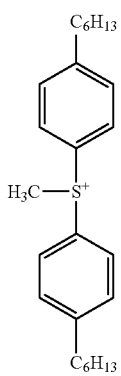

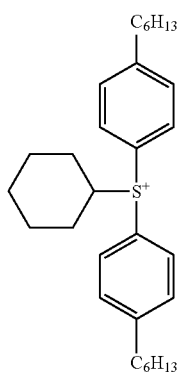

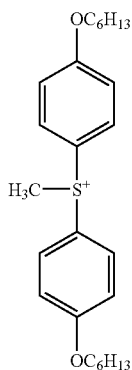

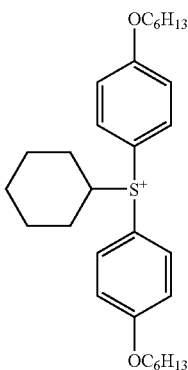

In Salt (I), $Q^1$ and $Q^2$ each independently represent a fluorine atom or a C1-C6 perfluoroalkyl group. Examples of the C1-C6 perfluoroalkyl group include a trifluoromethyl, pentafluoroethyl, heptafluoropropyl, nonafluorobutyl, undecafluoropentyl and tridecafluorohexyl group, and the trifluoromethyl group is preferable. It is preferred that $Q^1$ and $Q^2$ each independently represent the fluorine atom or the trifluoromethyl group, and it is more preferred that $Q^1$ and $Q^2$ represent the fluorine atoms.

In Salt (I), R represents
a group represented by the formula:

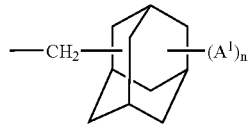

wherein $A^1$ represents —OH or —$Y^1$—OH, n represents an integer of 1 to 9, and $Y^1$ represents a divalent C1-C6 saturated aliphatic hydrocarbon group (hereinafter, simply referred to as the group (R-1)),
a group represented by the formula:

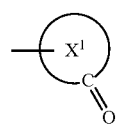

wherein ring $X^1$ represents a C3-C30 monocyclic or polycyclic hydrocarbon group in which one —CH$_2$— group is substituted with —CO—, and at least one hydrogen atom in the monocyclic or polycyclic hydrocarbon group may be substituted with a C1-C6 alkyl group, a C1-C6 alkoxy group, a C1-C4 perfluoroalkyl group, a C1-C6 hydroxyalkyl group, a hydroxyl group or a cyano group (hereinafter, simply referred to as the group (R-2)),
a group represented by the formula:

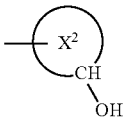

wherein ring $X^2$ represents a C3-C30 monocyclic or polycyclic hydrocarbon group in which a hydrogen atom of one —CH$_2$— group is substituted with a hydroxyl group, and at least one hydrogen atom in the monocyclic or polycyclic hydrocarbon group may be substituted with a C1-C6 alkyl group, a C1-C6 alkoxy group, a C1-C4 perfluoroalkyl group, a C1-C6 hydroxyalkyl group, a hydroxyl group or a cyano group (hereinafter, simply referred to as the group (R-3)),
a group represented by the formula:

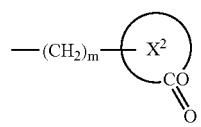

wherein ring $X^3$ represents a C3-C30 monocyclic or polycyclic hydrocarbon group in which one —CH$_2$— group is substituted with —COO—, and at least one hydrogen atom in the monocyclic or polycyclic hydrocarbon group may be substituted with a C1-C6 alkyl group, a C1-C6 alkoxy group, a C1-C4 perfluoroalkyl group, a C1-C6 hydroxyalkyl group, a hydroxyl group or a cyano group, and m represents an integer of 0 to 12 (hereinafter, simply referred to as the group (R-4)),
or a group represented by the formula:

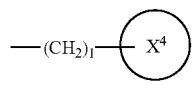

wherein ring $X^4$ represents a C6-C30 polycyclic hydrocarbon group having tricycle or more, and at least one hydrogen atom in the polycyclic hydrocarbon group may be substituted with a C1-C6 alkyl group, a C1-C6 alkoxy group, a C1-C4 perfluoroalkyl group, a C1-C6 hydroxyalkyl group or a cyano group, and l represents an integer of 1 to 12 (hereinafter, simply referred to as the group (R-5)).

When R is the group (R-1), Salt (I) is one represented by the following formula (Ia).

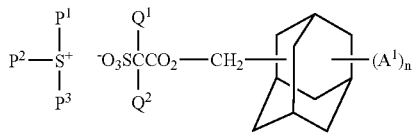
(Ia)

It is preferred that n is 1 or 2, because of the easiness of the production.

In the formula (Ia), $A^1$ represents —OH or —$Y^1$—OH and $Y^1$ represents a divalent C1-C6 saturated aliphatic hydrocarbon group. The divalent C1-C6 saturated aliphatic hydrocarbon group may be straight or branched chained. Examples of the divalent C1-C6 saturated aliphatic hydrocarbon group include the following formulae ($Y^1$-1) to ($Y^1$-12), and the formulae ($Y^1$-1) and ($Y^1$-2) are preferable because of the easiness of the production.

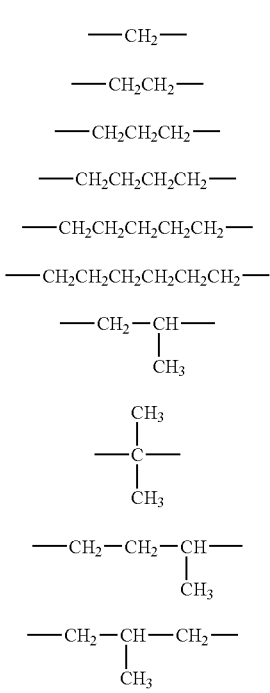

($Y^1$-1)
($Y^1$-2)
($Y^1$-3)
($Y^1$-4)
($Y^1$-5)
($Y^1$-6)
($Y^1$-7)
($Y^1$-8)
($Y^1$-9)
($Y^1$-10)

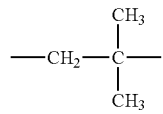
($Y^1$-11)

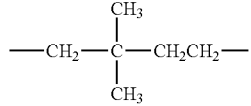
($Y^1$-12)

In the above formulae, the straight line with an open end shows a bond extended from an adjacent group.

It is preferred that $A^1$ is —OH, —$CH_2$—OH or —$CH_2CH_2$—OH, and it is more preferred that $A^1$ is —OH or —$CH_2$—OH.

Examples of the group (R-1) include the followings:

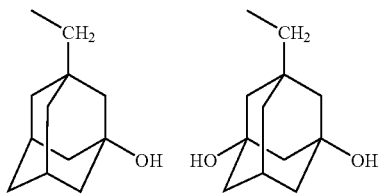

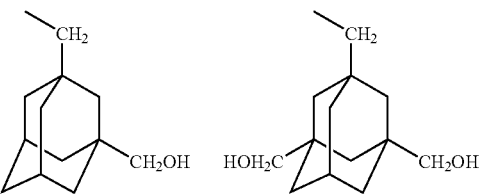

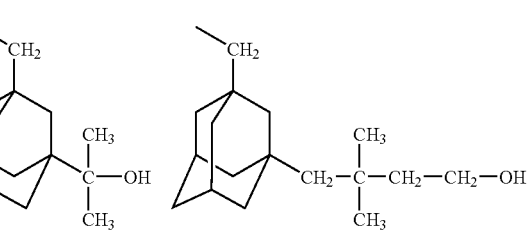

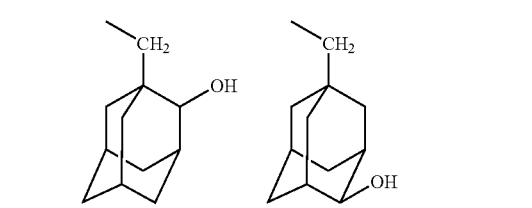

In the above formulae, the straight line with an open end shows a bond extended from an adjacent group.

Specific examples of the anion part of Salt (I) wherein R is the group (R-1) include the following anions:

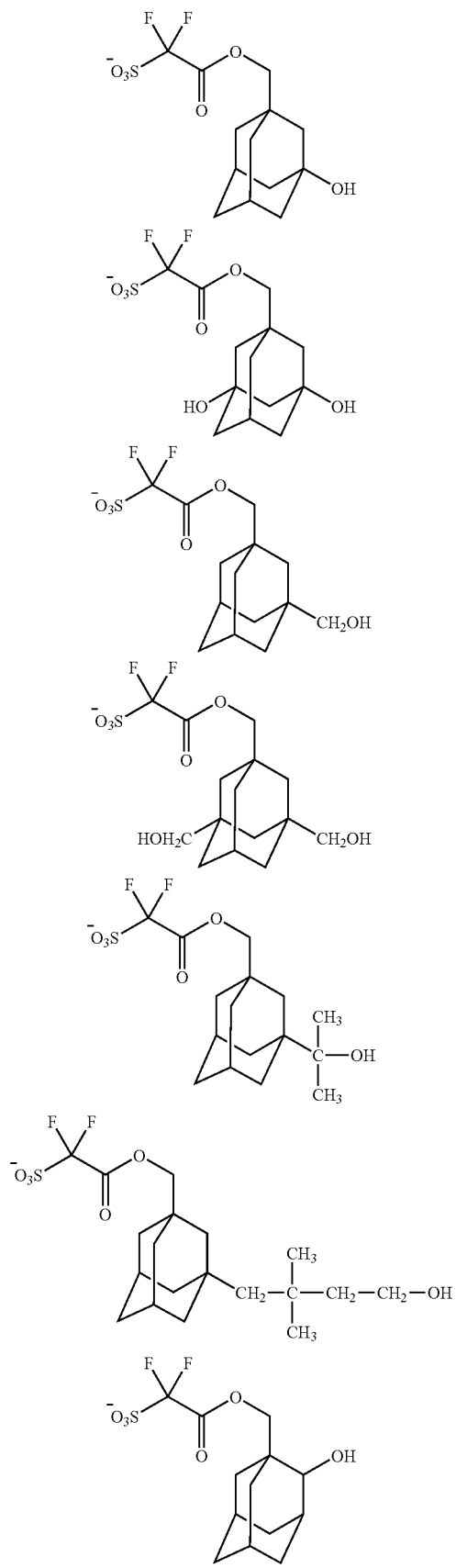
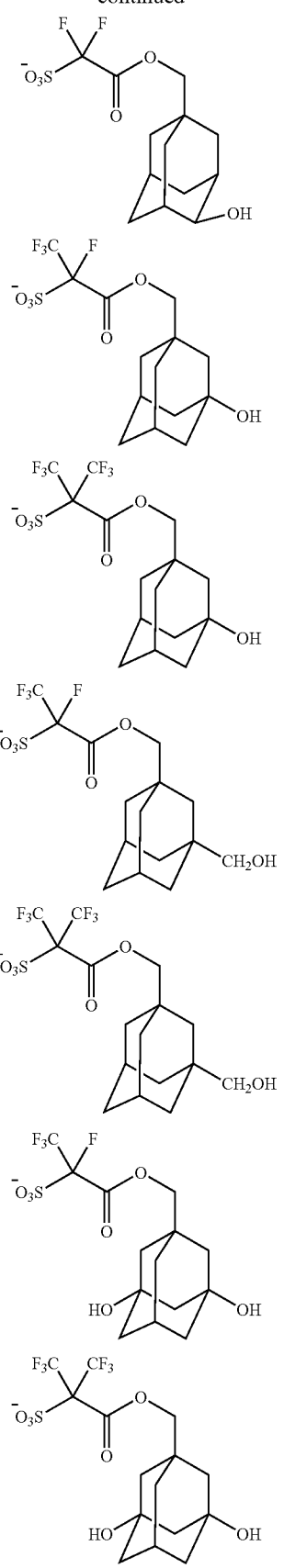
-continued

-continued

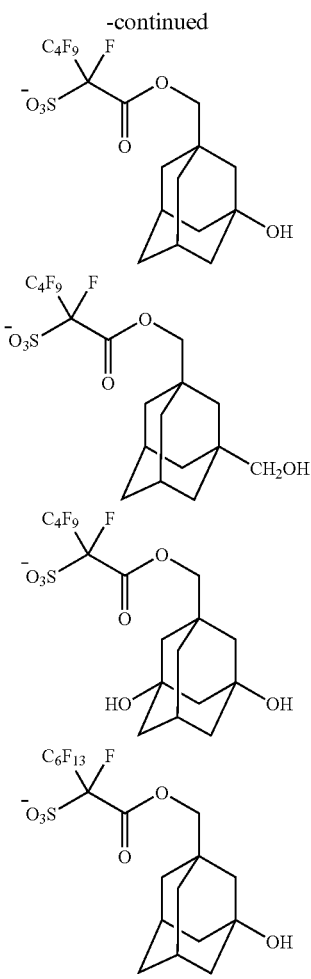

Preferred examples of Salt (I) wherein R is the group (R-1) include the following formulae (IVa), (IVb), (IVc) and (IVd):

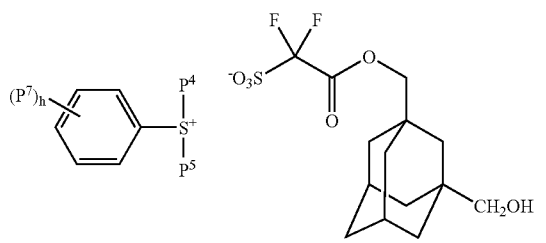
(IVa)

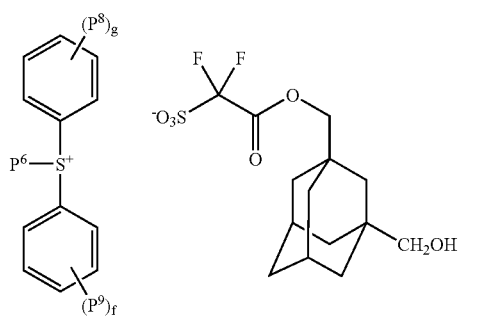
(IVb)

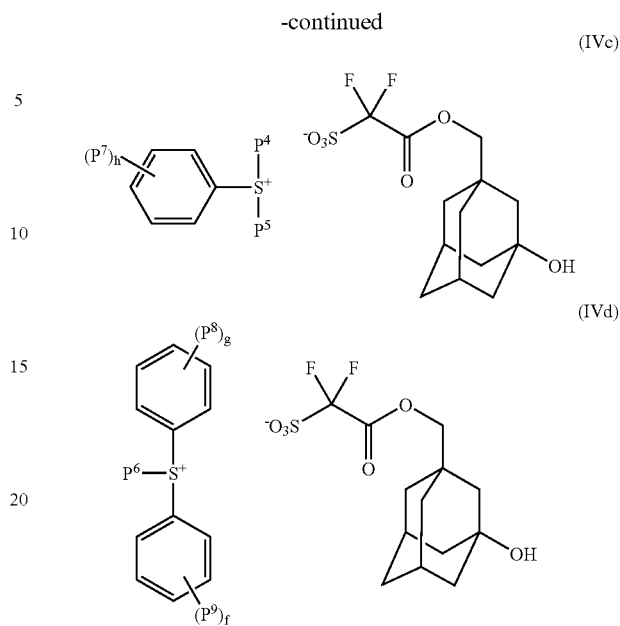
(IVc)
(IVd)

wherein $P^4$, $P^5$, $P^6$, $P^7$, $P^8$, $P^9$, f, g and h are the same as defined above.

When R is the group (R-2), Salt (I) is one represented by the following formula (Ib).

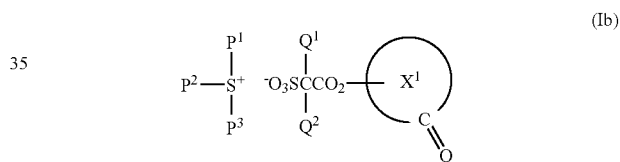
(Ib)

The ring $X^1$ represents a C3-C30 monocyclic or polycyclic hydrocarbon group in which one —$CH_2$— group is substituted with —CO—. At least one hydrogen atom in the monocyclic or polycyclic hydrocarbon group may be substituted with a C1-C6 alkyl group, a C1-C6 alkoxy group, a C1-C4 perfluoroalkyl group, a C1-C6 hydroxyalkyl group, a hydroxyl group or a cyano group.

Examples of the C1-C6 alkyl group include a methyl, ethyl, n-propyl, isopropyl, n-butyl, sec-butyl, tert-butyl, n-pentyl and n-hexyl group. Examples of the C1-C6 alkoxy group include a methoxy, ethoxy, n-propoxy, isopropoxy, n-butoxy, sec-butoxy, tert-butoxy, n-pentyloxy and n-hexyloxy group. Examples of the C1-C4 perfluoroalkyl group include a trifluoromethyl, pentafluoroethyl, heptafluoropropyl and nonafluorobutyl group. Examples of the C1-C6 hydroxyalkyl group include a hydroxymethyl, 2-hydroxyethyl, 3-hydroxypropyl, 4-hydroxybutyl and 6-hydroxyhexyl group.

Preferred examples of the ring $X^1$ include a C4-C8 oxocycloalkyl group such as an oxocyclopentyl and oxocyclohexyl group; an oxoadamantyl group; and an oxonorbornyl group, and at least one hydrogen atom in each of the groups may be substituted with the above-mentioned C1-C6 alkyl, C1-C6 alkoxy, C1-C4 perfluoroalkyl, C1-C6 hydroxyalkyl, hydroxyl or cyano group.

Specific examples of the group (R-2) include a 2-oxocyclopentyl group, a 2-oxocyclohexyl group, a 3-oxocyclopentyl group, a 3-oxocyclohexyl group, a 4-oxocyclohexyl group, a 4-oxo-1-adamantyl group, a 3-oxo-2-norbornyl group, a 1,7,7-trimethyl-2-oxo-3-norbornyl group, a 3,7,7-trimethyl-2-oxo-bicyclo[3.1.1]heptan-3-yl group, and the following groups:

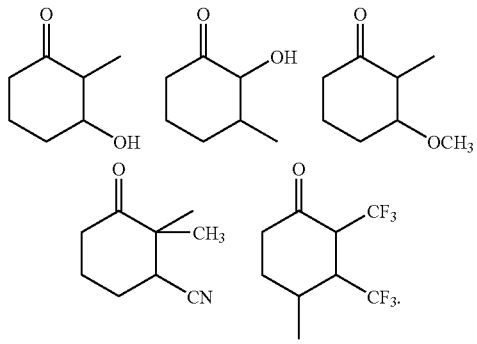

In the formulae above, straight line with an open end shows a bond which is extended from an adjacent group.

Specific examples of the anion part of Salt (I) wherein R is the group (R-2) include the following anions:

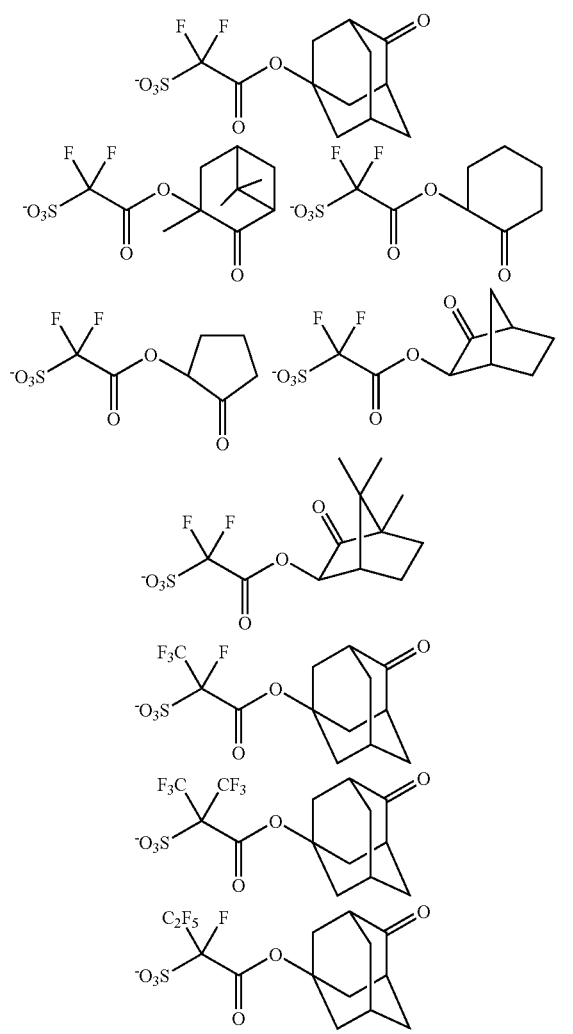

-continued

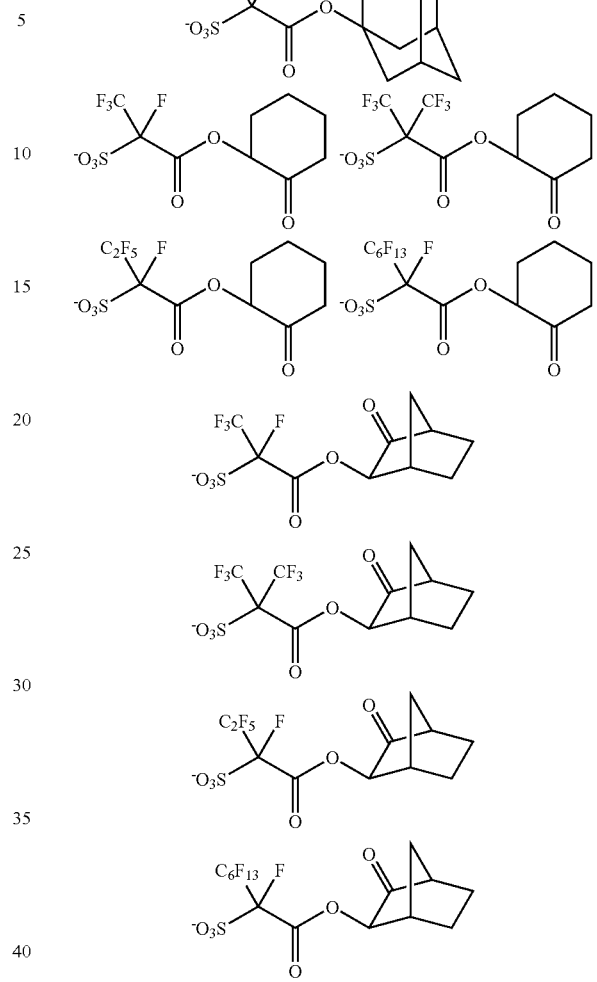

Preferred examples of Salt (I) wherein R is the group (R-2) include the following formulae (IVe) and (IVf):

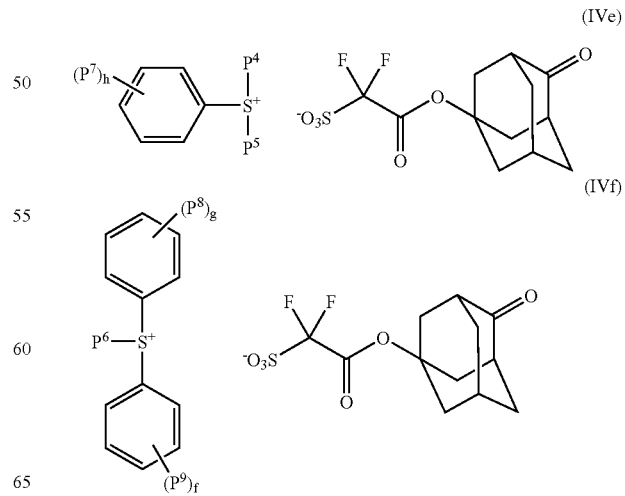

wherein $P^4$, $P^5$, $P^6$, $P^7$, $P^8$, $P^9$, f, g and h are the same as defined above.

When R is the group (R-3), Salt (I) is one represented by the following formula (Ic).

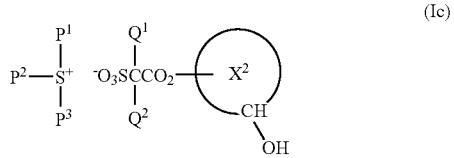
(Ic)

The ring $X^2$ represents a C3-C30 monocyclic or polycyclic hydrocarbon group in which a hydrogen atom of one —$CH_2$— group is substituted with a hydroxyl group. At least one hydrogen atom in the monocyclic or polycyclic hydrocarbon group may be substituted with a C1-C6 alkyl group, a C1-C6 alkoxy group, a C1-C4 perfluoroalkyl group, a C1-C6 hydroxyalkyl group, a hydroxyl group or a cyano group.

Examples of the C1-C6 alkyl group, the C1-C6 alkoxy group, the C1-C4 perfluoroalkyl group and the C1-C6 hydroxyalkyl group include the same as the same groups as mentioned in the group (R-2), respectively.

Preferred examples of the ring $X^2$ include a C4-C8 hydroxycycloalkyl group such as a hydroxycyclopentyl and hydroxycyclohexyl group; a hydroxyadamantyl group; and a hydroxynorbornyl group, and at least one hydrogen atom in each of the groups may be substituted with the above-mentioned C1-C6 alkyl, C1-C6 alkoxy, C1-C4 perfluoroalkyl, C1-C6 hydroxyalkyl, hydroxyl or cyano group.

Specific examples of the group (R-3) include a 2-hydroxycyclopentyl group, a 2-hydroxycyclohexyl group, a 3-hydroxycyclopentyl group, a 3-hydroxycyclohexyl group, a 4-hydroxycyclohexyl group, a 3-hydroxy-1-adamantyl group, a 4-hydroxy-1-adamantyl group, a 2-hydroxy-3-norbornyl group, a 1,7,7-trimethyl-2-hydroxy-3-norbornyl group, a 3,7,7-trimethyl-2-hydroxybicyclo[3.1.1]heptan-3-yl group, and the following groups:

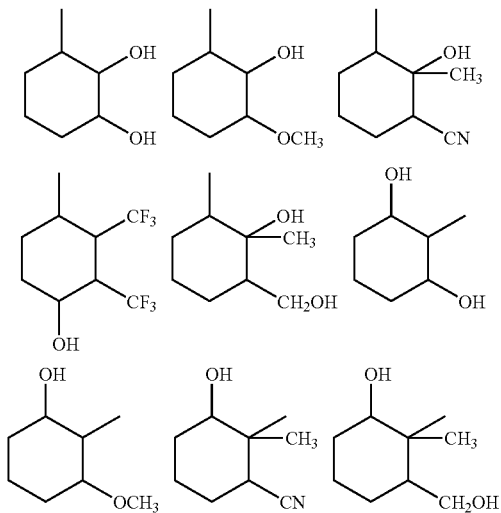

-continued

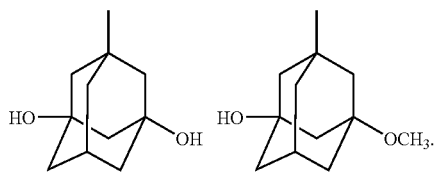

In the formulae above, straight line with an open end shows a bond which is extended from an adjacent group.

Specific examples of the anion part of Salt (I) wherein R is the group (R-3) include the following anions:

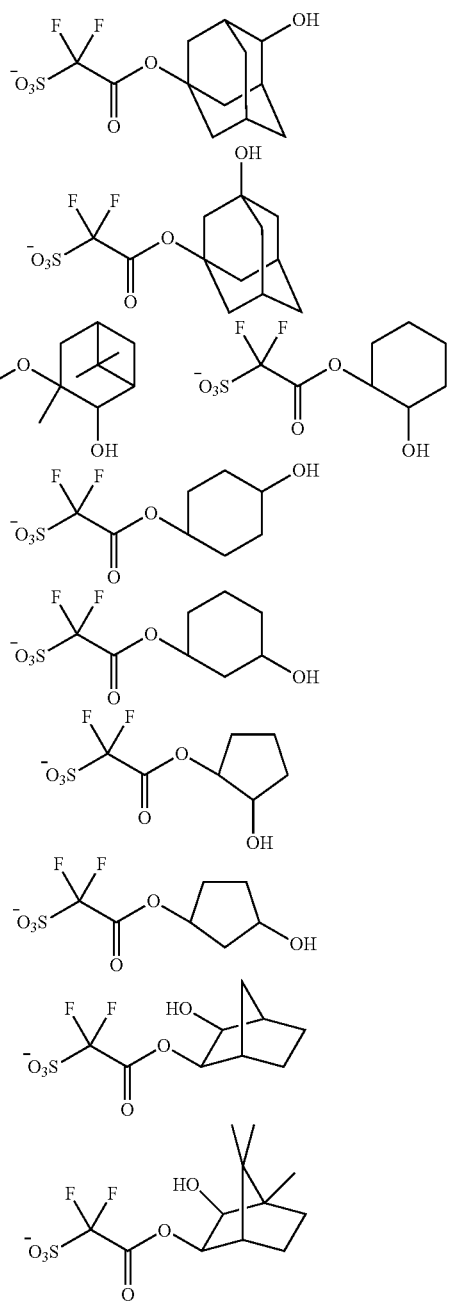

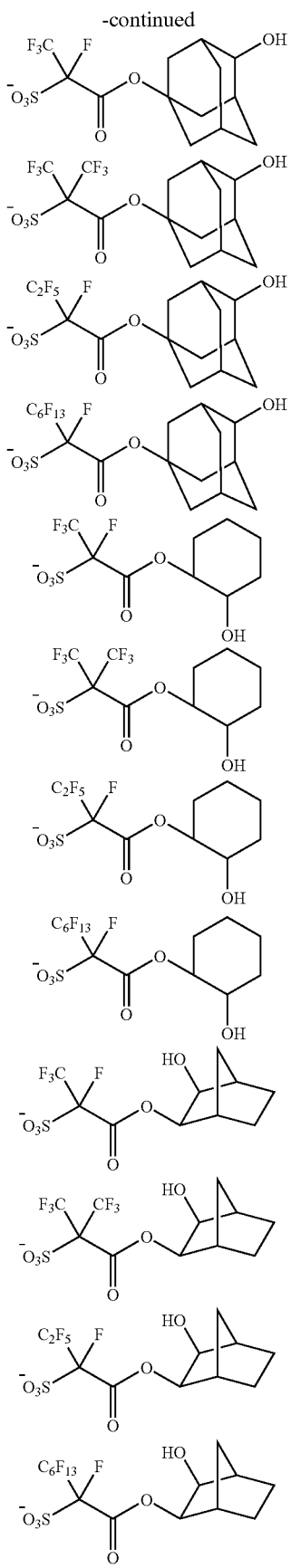
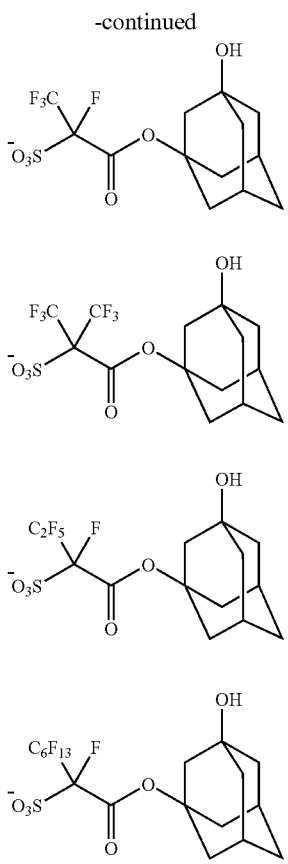
Preferred examples of Salt (I) wherein R is the group (R-3) include the following formulae (IVg) and (IVh):
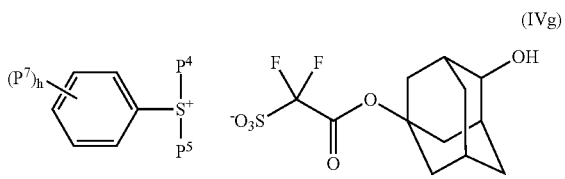
(IVg)
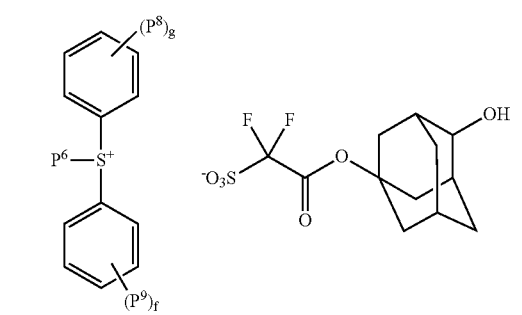
(IVh)
wherein $P^4$, $P^5$, $P^6$, $P^7$, $P^8$, $P^9$, f, g and h are the same as defined above.
When R is the group (R-4), Salt (I) is one represented by the following formula (Id).

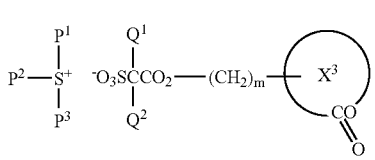
(Id)

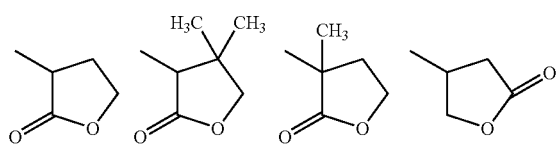

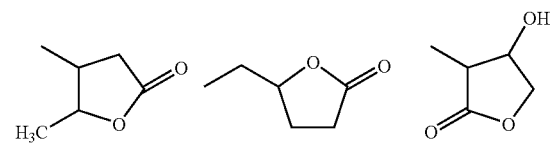

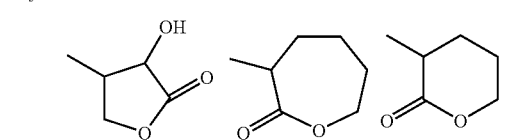

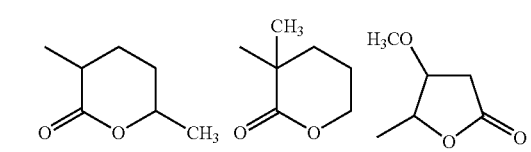

The ring $X^3$ represents a C3-C30 monocyclic or polycyclic hydrocarbon group in which one —$CH_2$— group is substituted with —COO—. At least one hydrogen atom in the monocyclic or polycyclic hydrocarbon group may be substituted with a C1-C6 alkyl group, a C1-C6 alkoxy group, a C1-C4 perfluoroalkyl group, a C1-C6 hydroxyalkyl group, a hydroxyl group or a cyano group, and m represents an integer of 0 to 12.

Examples of the C1-C6 alkyl group, the C1-C6 alkoxy group, the C1-C4 perfluoroalkyl group and the C1-C6 hydroxyalkyl group include the same as the same groups as mentioned in the group (R-2), respectively.

Examples of the ring $X^3$ include a monovalent residue of a compound represented by the formula (IIa), (IIb) or (IIc).

(IIa)

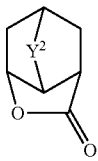
(IIb)

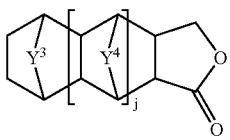
(IIc)

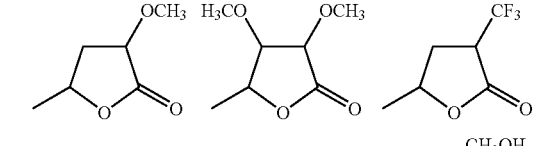

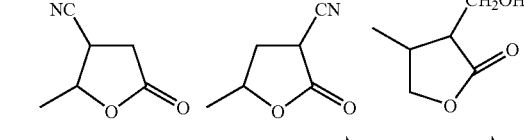

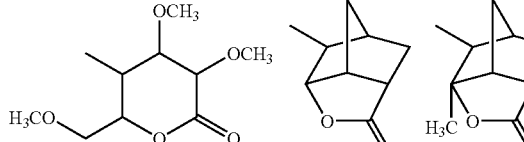

The monovalent residue of a compound represented by the formula (IIa) or (IIb) is preferable.

In the formulae (IIa), (IIb) and (IIc), $Y^2$, $Y^3$ and $Y^4$ each independently represent (a) an alkylene group or (b) no bonding and a hydrogen atom in each side, k represents an integer of 1 to 4, j represents an integer of 0 to 2, and at least one hydrogen atom in the formulae (IIIa), (IIIb) and (IIIc) may be substituted with a C1-C6 alkyl group, a C1-C6 alkoxy group, a C1-C4 perfluoroalkyl group, a C1-C6 hydroxyalkyl group, a hydroxyl group or a cyano group.

Examples of the alkylene group in $Y^2$, $Y^3$ and $Y^4$ include a methylene, ethylene and propane-2,2-diyl group, and the methylene and propane-2,2-diyl group are preferable.

"No bonding and a hydrogen atom in each side" means bridge —$Y^2$—, —$Y^3$— or —$Y^4$— does not exist and the hydrogen atom is bonded in each side of the position of —$Y^2$—, —$Y^3$— or —$Y^4$—.

It is preferred that k is an integer of 2 to 4.

Specific examples of the monovalent residue of compound shown by the formula (IIa), (IIb) or (IIc) include the followings.

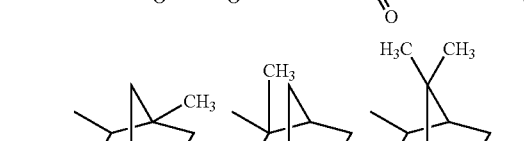

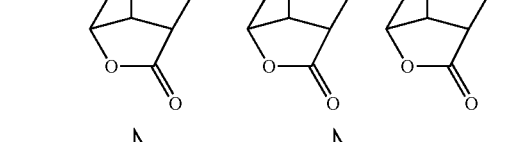

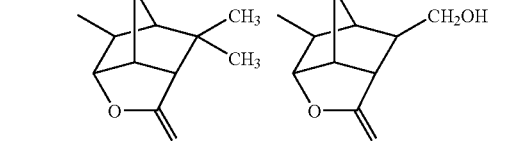

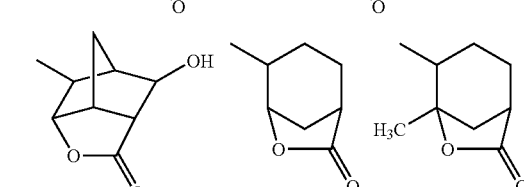

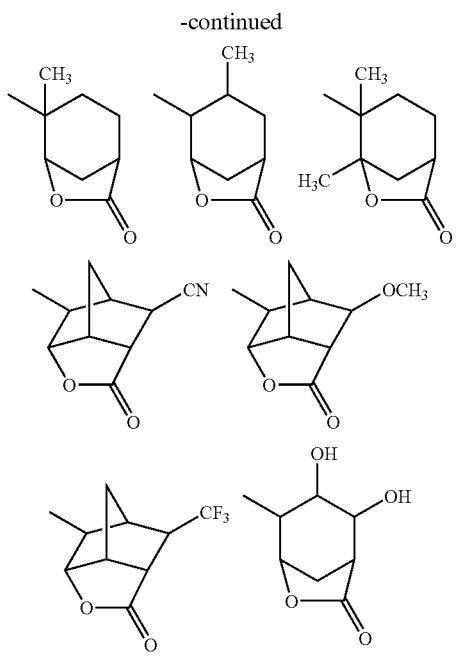
In the formulae above, straight line with an open end shows a bond which is extended from an adjacent group.
Specific examples of anion part of the salt (I) wherein R is the group (R-4) include the followings.
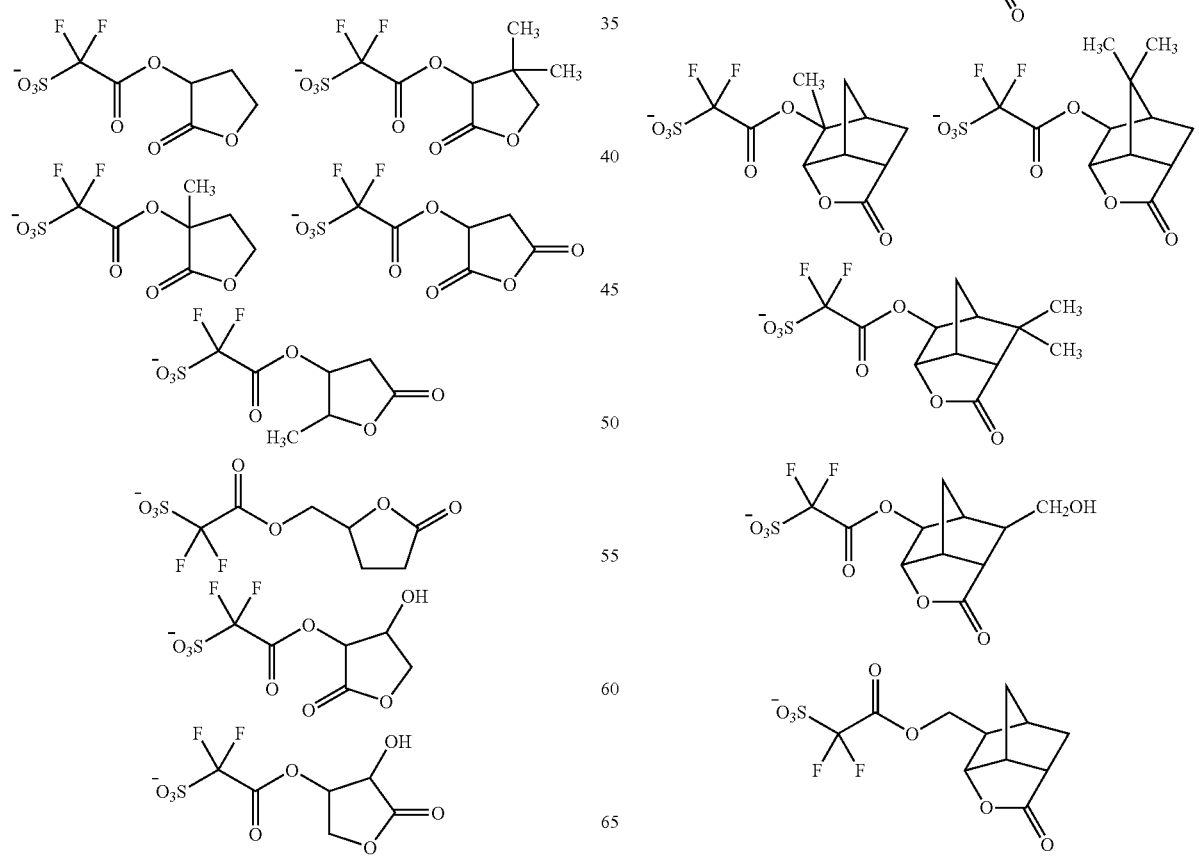
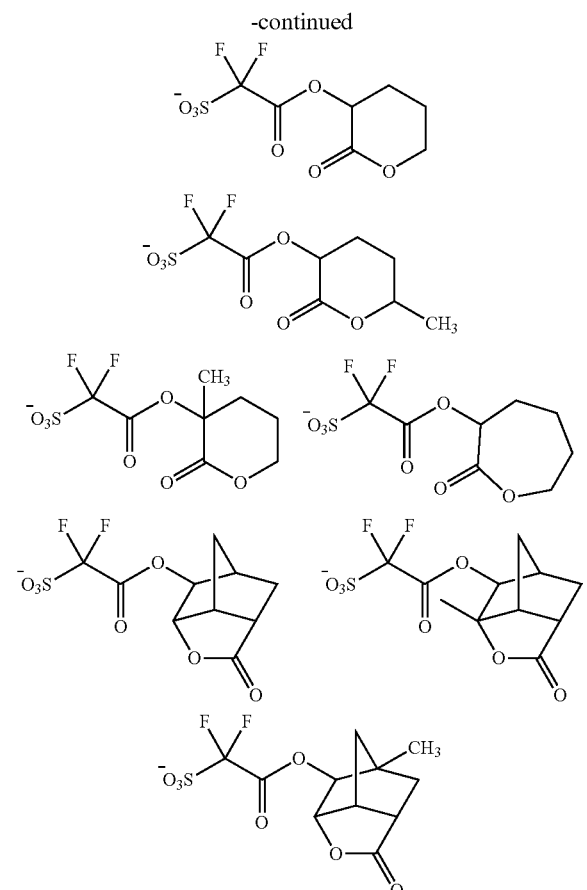

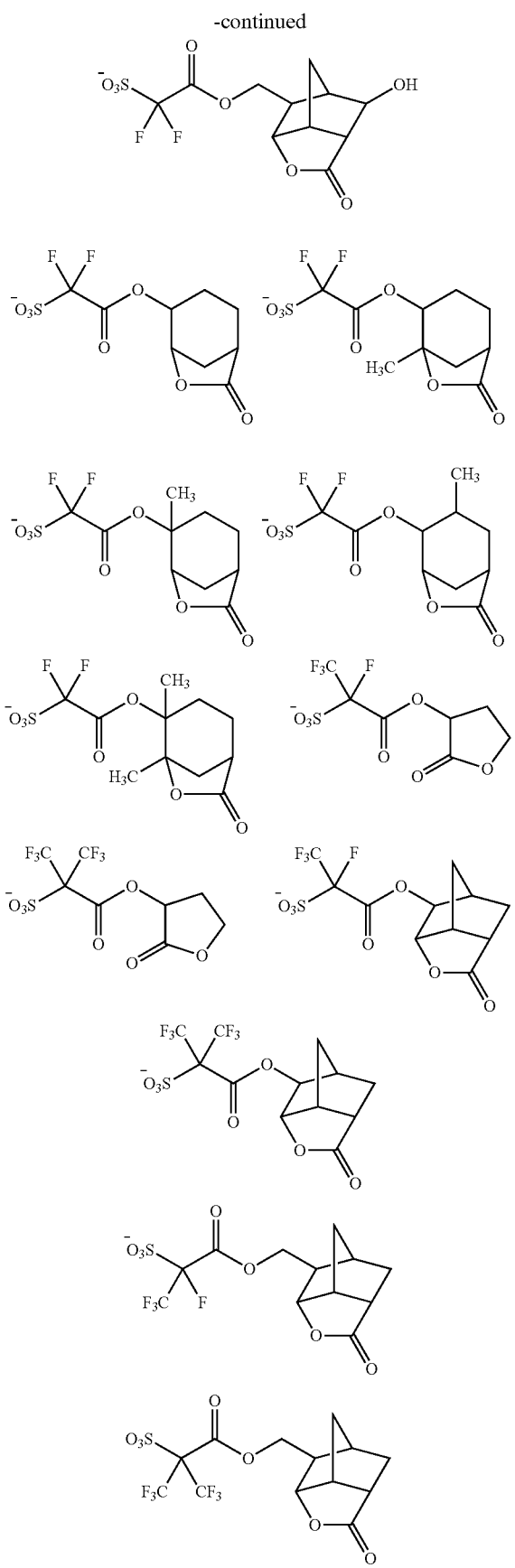
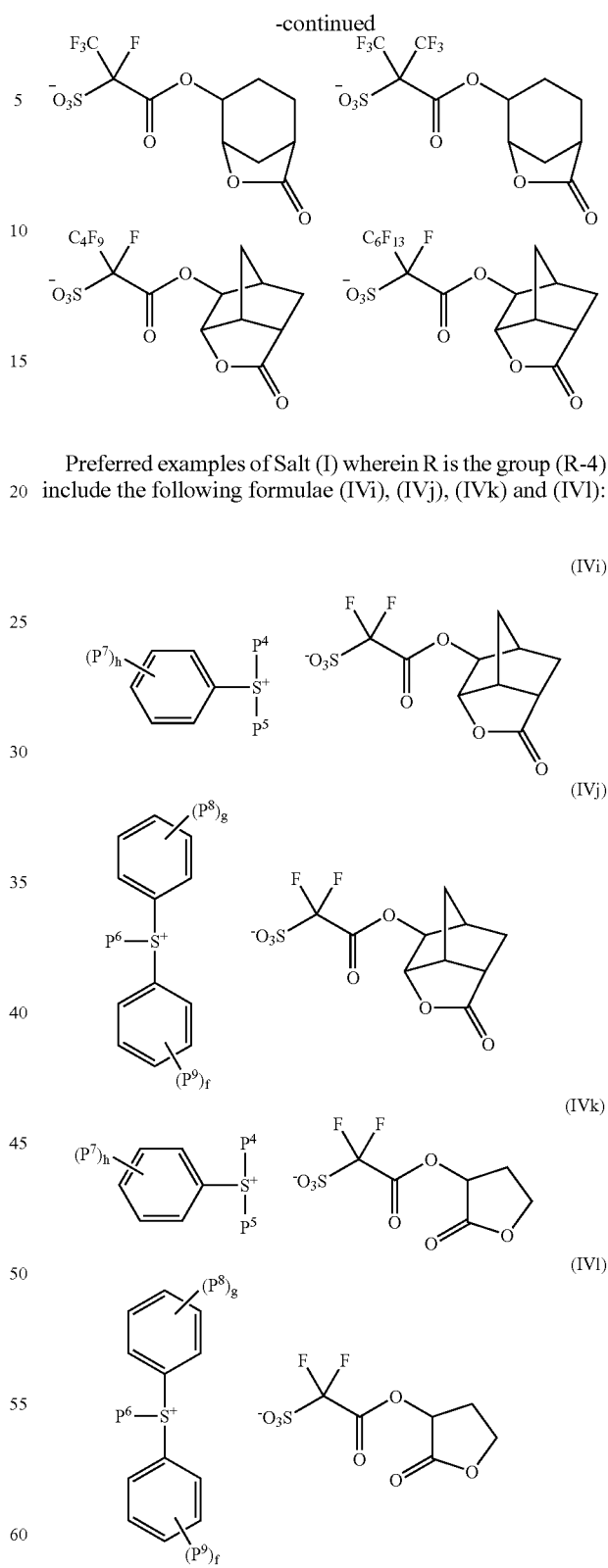
Preferred examples of Salt (I) wherein R is the group (R-4) include the following formulae (IVi), (IVj), (IVk) and (IVl):
wherein $P^4$, $P^5$, $P^6$, $P^7$, $P^8$, $P^9$, f, g and h are the same as defined above.
When R is the group (R-5), Salt (I) is one represented by the following formula (Ie).

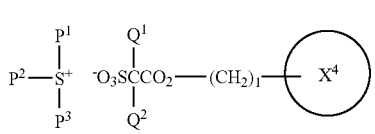
(Ie)

The ring $X^4$ represents a C6-C30 polycyclic hydrocarbon group having tricycle or more. The polycyclic hydrocarbon group has preferably 10 to 30 carbon atoms. At least one hydrogen atom in the polycyclic hydrocarbon group may be substituted with a C1-C6 alkyl group, a C1-C6 alkoxy group, a C1-C4 perfluoroalkyl group, a C1-C6 hydroxyalkyl group or a cyano group, and l represents an integer of 1 to 12, preferably an integer of 1 to 6 and more preferably an integer of 1 to 2.

Examples of the C1-C6 alkyl group, the C1-C6 alkoxy group, the C1-C4 perfluoroalkyl group and the C1-C6 hydroxyalkyl group include the same as the same groups as mentioned in the group (R-2), respectively.

The ring $X^4$ is preferably a tricyclic, tetracyclic, pentacyclic or hexacyclic hydrocarbon group having 10 to 20 carbon atoms. One or more hydrogen atoms in the tricyclic, tetracyclic, pentacyclic or hexacyclic hydrocarbon group may be substituted with the above-mentioned C1-C6 alkyl group, the above-mentioned C1-C6 alkoxy group, the above-mentioned C1-C4 perfluoroalkyl group, the above-mentioned C1-C6 hydroxyalkyl group or the cyano group.

More preferred examples of the ring $X^4$ include a monovalent residue of a compound represented by the following formula (IIIa) or (IIIb), and especially preferred is the monovalent residue of a compound represented by the following formula (IIIa).

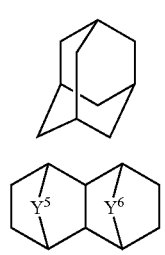

(IIIa)

(IIIb)

$Y^5$ represents (a) an alkylene group or (b) an oxygen atom (—O—). Examples of the alkylene group include a methylene and ethylene group.

$Y^6$ represents (a) an alkylene group, (b) an oxygen atom (—O—) or (c) no bonding and hydrogen atom in each side. Examples of the alkylene group include the same as the same groups as mentioned in the $Y^5$. "No bonding and a hydrogen atom in each side" means bridge —$Y^6$— does not exist and the hydrogen atom is bonded in each side of the position of —$Y^6$—.

One or more hydrogen atoms in the formulae (IIIa) and (IIIb) may be substituted with the above-mentioned C1-C6 alkyl group, the above-mentioned C1-C6 alkoxy group, the above-mentioned C1-C4 perfluoroalkyl group or the cyano group.

Specific examples of the monovalent residue of the compound represented by the formula (IIIa) or (IIIb) include the followings:

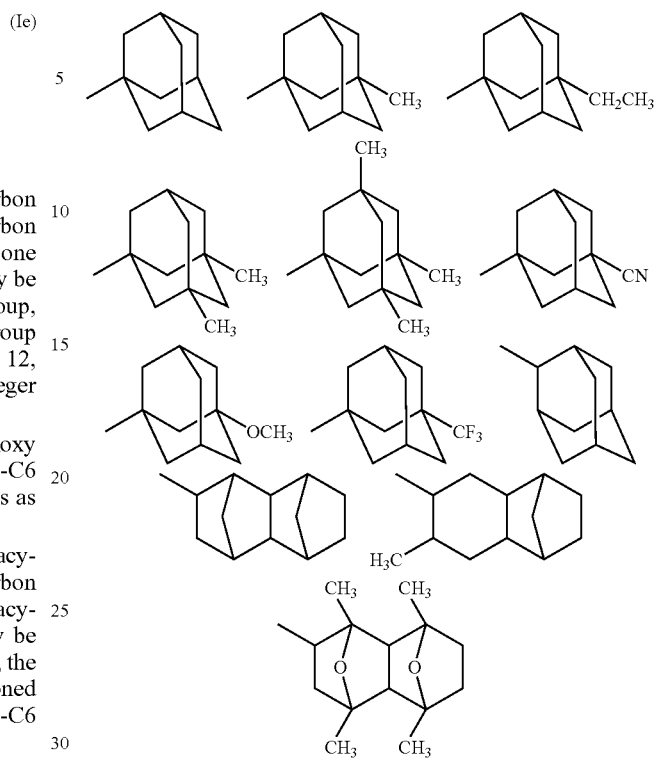

In the formulae above, straight line with an open end shows a bond which is extended from an adjacent group.

Examples of the group (R-5) include the followings.

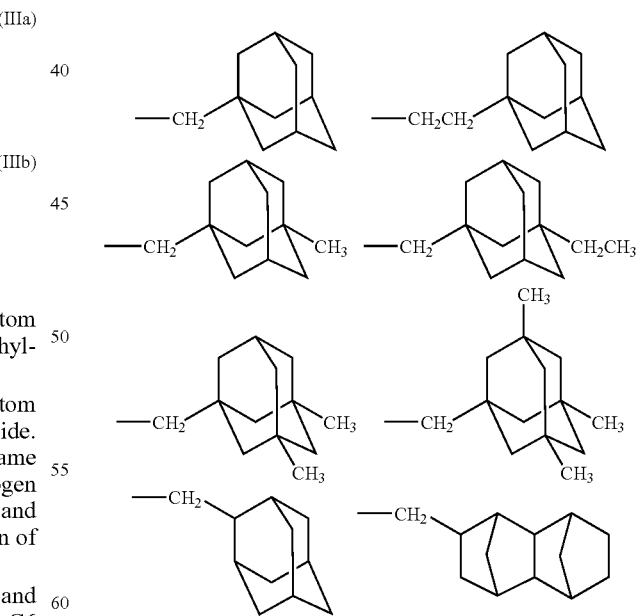

In the formulae above, straight line with an open end shows a bond which is extended from an adjacent group.

Specific examples of the anion part of Salt (I) wherein R is the group (R-5) include the followings.

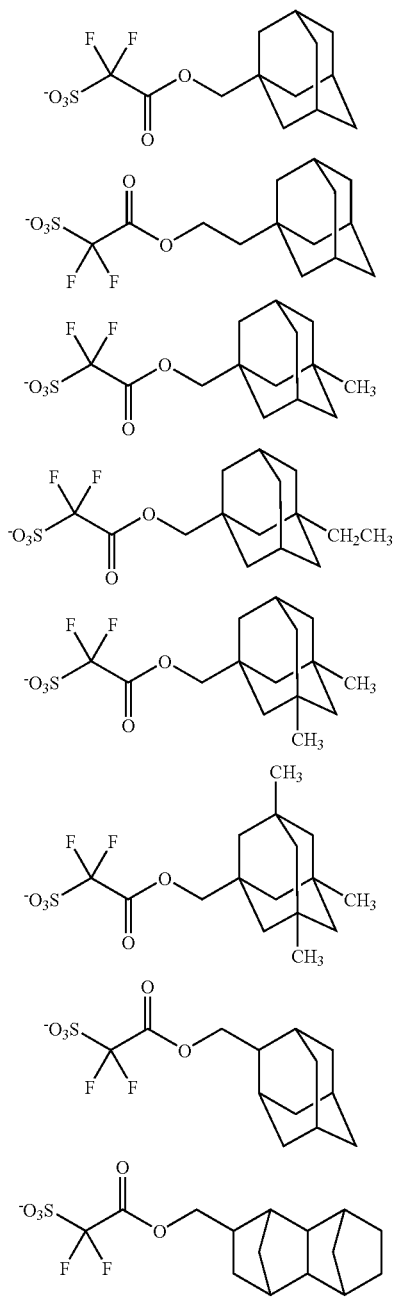

Preferred examples of Salt (I) wherein R is the group (R-5) include the following formulae (IVm) and (IVn):

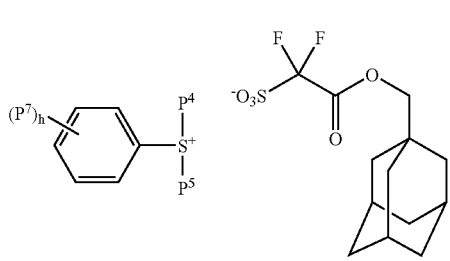

(IVm)

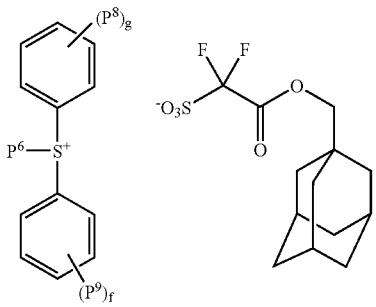

(IVn)

wherein $P^4$, $P^5$, $P^6$, $P^7$, $P^8$, $P^9$, f, g and h are the same as defined above.

Examples of the process for production of Salt (I) include a process comprising reacting a compound represented by the formula (V):

$$R\text{—}OH \qquad (V)$$

wherein R is the same as defined above (hereinafter, simply referred to as the compound (V)), with a salt represented by the formula (VI):

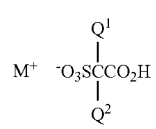

(VI)

wherein $Q^1$ and $Q^2$ are the same as defined above, and M represents Li, Na, K or Ag (hereinafter, simply referred to as the salt (VI)), to obtain a salt represented by the formula (VII):

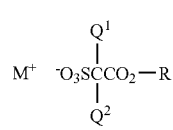

(VII)

wherein R, $Q^1$, $Q^2$ and M are the same as defined above (hereinafter, simply referred to as the salt (VII)), and reacting the salt (VII) obtained with a compound represented by the formula (VIII):

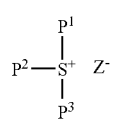

(VIII)

wherein $P^1$, $P^2$ and $P^3$ are the same as defined above and Z represents F, Cl, Br, I, $BF_4$, $AsF_6$, $SbF_6$, $PF_6$ or $ClO_4$ (hereinafter, simply referred to as the compound (VIII)).

As the compound (V), commercially available one is usually used.

The reaction of the compound (V) and the salt (VI) can be usually conducted by mixing materials in an aprotic solvent such as dichloroethane, toluene, ethylbenzene, monochlorobenzene, acetonitrile and N,N-dimethylformamide, at 20 to 200° C., preferably 50 to 150° C. The reaction can be usually carried out in the presence of an acid or a dehydrating agent. Examples of the acid catalyst include an organic acid such as p-toluenesulfonic acid and an inorganic acid such as sulfuric acid. Examples of the dehydrating agent include 1,1'-carbonyldiimidazole and N,N'-dicyclohexylcarbodiimide.

The reaction of the compound (V) and the salt (VI) may also preferably be conducted while removing water generated, for example, by Dean Stark method as the reaction time tends to be shortened.

The amount of the salt (VI) to be used is usually 0.2 to 5 moles, preferably 0.5 to 2 moles relative to 1 mole of the compound (V). The amount of the acid catalyst to be used may be catalytic amount or the amount equivalent to solvent, and it is usually 0.001 to 5 moles, preferably 0.001 to 3 moles relative to 1 mole of the compound (V). The amount of the dehydrating agent to be used is usually 0.2 to 5 moles, preferably 0.5 to 2 moles relative to 1 mole of the compound (V).

The reaction of the salt (VII) obtained and the compound (VIII) is conducted in an inert solvent such as acetonitrile, water, methanol, chloroform and dichloromethane, at a temperature of 0 to 150° C., preferably of 0 to 100° C.

The amount of the compound (VIII) to be used is usually 0.5 to 2 moles relative to 1 mole of the salt (VII). Salt (I) obtained may be isolated from the reaction mixture by extraction and concentration of the organic layer obtained.

Next, the present chemically amplified positive resist composition will be illustrated.

The present chemically amplified positive resist composition comprises Salt (I) and a resin containing a structural unit which has an acid-labile group and which itself is insoluble or poorly soluble in an aqueous alkali solution but becomes soluble in an aqueous alkali solution by the action of an acid.

Salt (I) is usually used as an acid generator, and the acid generated by irradiation to Salt (I) catalytically acts against acid-labile groups in the resin, cleaves acid-labile groups, and the resin becomes soluble in an alkali aqueous solution. Such a composition is suitable for chemically amplified positive resist composition.

The resin used for the present composition contains a structural unit which has the acid-labile group and which itself is insoluble or poorly soluble in an alkali aqueous solution, but the acid-labile group cleave by an acid.

In the present specification, "—COOR" may be described as "a structure having ester of carboxylic acid", and may also be abbreviated as "ester group". Specifically, "—COOC(CH$_3$)$_3$" may be described as "a structure having tert-butyl ester of carboxylic acid", or be abbreviated as "tert-butyl ester group".

Examples of the acid-labile group include a structure having ester of carboxylic acid such as alkyl ester group in which a carbon atom adjacent to the oxygen atom is quaternary carbon atom, alicyclic ester group in which a carbon atom adjacent to the oxygen atom is quaternary carbon atom, and a lactone ester group in which a carbon atom adjacent to the oxygen atom is quaternary carbon atom. The "quaternary carbon atom" means a "carbon atom joined to four substituents other than hydrogen atom".

Examples of the acid-labile group include an alkyl ester group in which a carbon atom adjacent to the oxygen atom is quaternary carbon atom such as a tert-butyl ester group; an acetal type ester group such as a methoxymethyl ester, ethoxymethyl ester, 1-ethoxyethyl ester, 1-isobutoxyethylester, 1-isopropoxyethylester, 1-ethoxypropoxyester, 1-(2-methoxyethoxy)ethyl ester, 1-(2-acetoxyethoxy)ethyl ester, 1-[2-(1-adamantyloxy)ethoxy]ethyl ester, 1-[2-(1-adamantanecarbonyloxy)ethoxy]ethyl ester, tetrahydro-2-furyl ester and tetrahydro-2-pyranyl ester group; an alicyclic ester group in which a carbon atom adjacent to the oxygen atom is quaternary carbon atom, such as an isobornyl ester, 1-alkylcycloalkyl ester, 2-alkyl-2-adamantyl ester and 1-(1-adamantyl)-1-alkylalkyl ester group. At least one hydrogen atom in the adamantyl group may be substituted with a hydroxyl group.

Examples of the structural unit include a structure unit derived from an ester of acrylic acid, a structural unit derived from an ester of methacrylic acid, a structural unit derived from an ester of norbornenecarboxylic acid, a structural unit derived from an ester of tricyclodecenecarboxylic acid and a structural unit derived from an ester of tetracyclodecenecarboxylic acid. The structure units derived from the ester of acrylic acid and from the ester of methacrylic acid are preferable.

The resin used for the present composition can be obtained by conducting polymerization reaction of a monomer or monomers having the acid-labile group and an olefinic double bond.

Among the monomers, those having a bulky and acid-labile group such as an alicyclic ester group (e.g. a 2-alkyl-2-adamantyl ester and 1-(1-adamantyl)-1-alkylalkyl ester group), is preferred, since excellent resolution is obtained when the resin obtained is used in the present composition.

Examples of such monomer containing the bulky and acid-labile group include a 2-alkyl-2-adamantyl acrylate, a 2-alkyl-2-adamantyl methacrylate, 1-(1-adamantyl)-1-alkylalkyl acrylate, a 1-(1-adamantyl)-1-alkylalkyl methacrylate, a 2-alkyl-2-adamantyl 5-norbornene-2-carboxylate, a 1-(1-adamantyl)-1-alkylalkyl 5-norbornene-2-carboxylate, a 2-alkyl-2-adamantyl α-chloroacrylate and a 1-(1-adamantyl)-1-alkylalkyl α-chloroacrylate.

Particularly when the 2-alkyl-2-adamantyl acrylate, the 2-alkyl-2-adamantyl methacrylate or the 2-alkyl-2-adamantyl α-chloroacrylate is used as the monomer for the resin component in the present composition, a resist composition having excellent resolution tend to be obtained. Typical examples thereof include 2-methyl-2-adamantyl acrylate, 2-methyl-2-adamantyl methacrylate, 2-ethyl-2-adamantyl acrylate, 2-ethyl-2-adamantyl methacrylate, 2-n-butyl-2-adamantylacrylate, 2-methyl-2-adamantyl α-chloroacrylate and 2-ethyl-2-adamantyl α-chloroacrylate. When particularly 2-ethyl-2-adamantyl acrylate, 2-ethyl-2-adamantyl methacrylate, 2-isopropyl-2-adamantyl acrylate or 2-isopropyl-2-adamantyl methacrylate is used for the present composition, a resist composition having excellent sensitivity and heat resistance tends to be obtained. In the present invention, two or more kinds of monomers having a group or groups dissociated by the action of the acid may be used together, if necessary.

The 2-alkyl-2-adamantyl acrylate can be usually produced by reacting a 2-alkyl-2-adamantanol or a metal salt thereof with an acrylic halide, and the 2-alkyl-2-adamantyl methacrylate can be usually produced by reacting a 2-alkyl-2-adamantanol or a metal salt thereof with a methacrylic halide.

The resin used for the present composition can also contain other structural unit or units derived from an acid-stable monomer in addition to the above-mentioned structural units having the acid-labile group. Herein, the "structural unit derived from an acid-stable monomer" means "a structural unit not dissociated by an acid generated from Salt (I)".

Examples of such other structural unit derived from the acid-stable monomer include a structural unit derived from a monomer having a free carboxyl group such as acrylic acid and methacrylic acid; a structural unit derived from an aliphatic unsaturated dicarboxylic anhydride such as maleic anhydride and itaconic anhydride; a structural unit derived from 2-norbornene; a structural unit derived from acrylonitrile or methacrylonitrile; a structural unit derived from an alkyl acrylate or an alkyl methacrylate in which a carbon atom adjacent to oxygen atom is secondary or tertiary carbon atom; a structural unit derived from 1-adamantyl acrylate or 1-adamantyl methacrylate; a structural unit derived from styrene monomer such as p-hydroxystyrene and m-hydroxystyrene; a structural unit derived from acryloyloxy-γ-butyrolactone or methacryloyloxy-γ-butyrolactone having a lactone ring which may be substituted with an alkyl group; and the like. Herein, the 1-adamantyloxy carbonyl group is the acid-stable group though the carbon atom adjacent to oxygen atom is the quaternary carbon atom, and the 1-adamantyloxycarbonyl group may be substituted with at least one hydroxyl group.

Specific examples of the structural unit derived from the acid-stable monomer include a structural unit derived from 3-hydroxy-1-adamantyl acrylate;

a structural unit derived from 3-hydroxy-1-adamantyl methacrylate;

a structural unit derived from 3,5-dihydroxy-1-adamantyl acrylate;

a structural unit derived from 3,5-dihydroxy-1-adamantyl methacrylate;

a structural unit derived from α-acryloyloxy-γ-butyrolactone;

a structural unit derived from α-methacryloyloxy-γ-butyrolactone;

a structural unit derived from β-acryloyloxy-γ-butyrolactone;

a structural unit derived from β-methacryloyloxy-γ-butyrolactone;

a structural unit represented by the formula (X):

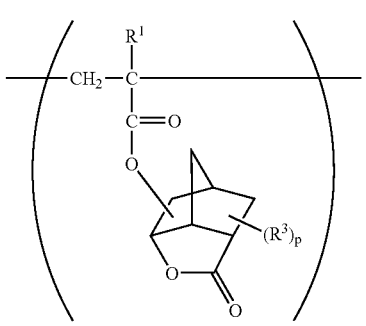

(X)

wherein $R^1$ represents a hydrogen atom or a methyl group, $R^3$ represents a methyl group, a trifluoromethyl group or a halogen atom, p represents an integer of 0 to 3, and when p represents 2 or 3, $R^3$s may be the same or different each other;

a structural unit represented by the formula (XI):

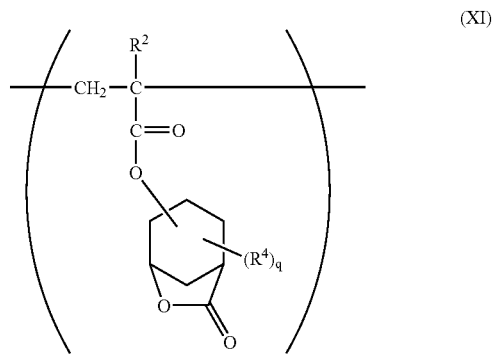

(XI)

wherein $R^2$ represents a hydrogen atom or a methyl group, $R^4$ represents a methyl group, a trifluoromethyl group or a halogen atom, q represents an integer of 0 to 3, and when q represents 2 or 3, $R^4$s may be the same or different each other;

a structural unit derived from p-hydroxystyrene;

a structural unit derived from m-hydroxystyrene;

a structural unit derived from an alicyclic compound having an olefinic double bond such as a structural unit represented by the formula (XII):

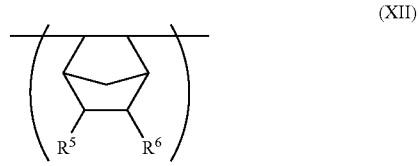

(XII)

wherein $R^5$ and $R^6$ each independently represents a hydrogen atom, a C1-C3 alkyl group, a C1-C3 hydroxyalkyl group, a carboxyl group, a cyano group or a —COOU group in which U represents an alcohol residue, or $R^5$ and $R^6$ can be bonded together to form a carboxylic anhydride residue represented by —C(=O)OC(=O)—;

a structural unit derived from an aliphatic unsaturated dicarboxylic anhydride such as a structural unit represented by the formula (XIII):

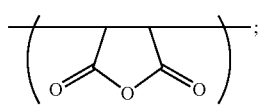

(XIII)

a structural unit represented by the formula (XIV):

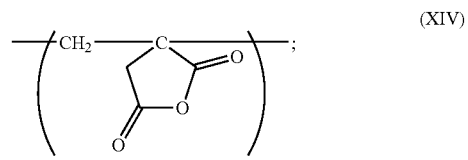

(XIV)

and the like.

Particularly, the resin having further at least one structural unit selected from the structural unit derived from p-hydroxystyrene, the structural unit derived from m-hydroxystyrene, the structural unit derived from 3-hydroxy-1-adamantyl acrylate, the structural unit derived from 3-hydroxy-1-adamantyl methacrylate, the structural unit derived from 3,5-dihydroxy-1-adamantyl acrylate, the structural unit derived from 3,5-dihydroxy-1-adamantyl methacrylate, the structural unit represented by the formula (X) and the structural unit represented by the formula (XI) in addition to the structural unit having the acid-labile group is preferable from the standpoint of the adhesiveness of resist to a substrate and resolution of resist.

3-Hydroxy-1-adamantyl acrylate, 3-hydroxy-1-adamantyl methacrylate, 3,5-dihydroxy-1-adamantyl acrylate and 3,5-dihydroxy-1-adamantyl methacrylate can be produced, for example, by reacting the corresponding hydroxyadamantane with acrylic acid, methacrylic acid or its acid halide, and they are also commercially available.

Further, the acryloyloxy-γ-butyrolactone and the methacryloyloxy-γ-butyrolactone having the lactone ring which may be substituted with the alkyl group can be produced by reacting corresponding α- or β-bromo-γ-butyrolactone with acrylic acid or methacrylic acid, or reacting corresponding α- or β-hydroxy-γ-butyrolactone with the acrylic halide or the methacrylic halide.

As monomers to give structural units represented by the formulae (X) and (XI), specifically listed are, for example, an acrylate of alicyclic lactones and a methacrylate of alicyclic lactones having the hydroxyl group described below, and mixtures thereof. These esters can be produced, for example, by reacting the corresponding alicyclic lactone having the hydroxyl group with acrylic acid or methacrylic acid, and the production method thereof is described in, for example, JP 2000-26446 A.

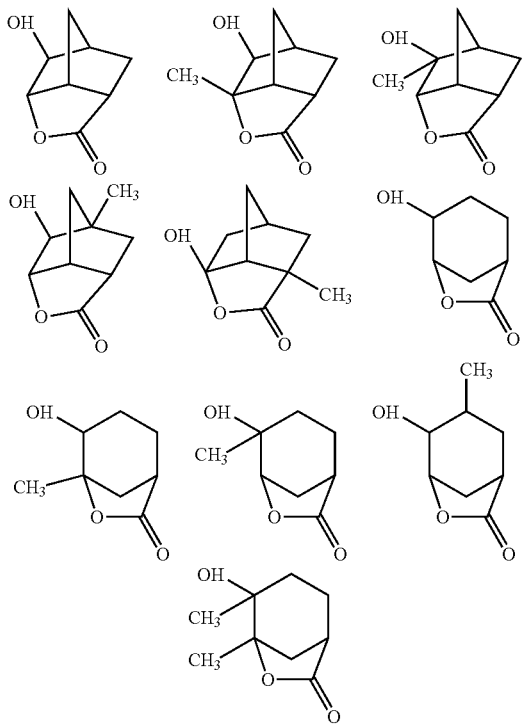

Examples of the acryloyloxy-γ-butyrolactone and the methacryloyloxy-γ-butyrolactone having the lactone ring which may be substituted with the alkyl group include α-acryloyloxy-γ-butyrolactone, α-methacryloyloxy-γ-butyrolactone, α-acryloyloxy-β,β-dimethyl-γ-butyrolactone, α-methacryloyloxy-β,β-dimethyl-γ-butyrolactone, α-acryloyloxy-α-methyl-γ-butyrolactone, α-methacryloyloxy-α-methyl-γ-butyrolactone, β-acryloyloxy-γ-butyrolactone, β-methacryloyloxy-γ-butyrolactone and β-methacryloyloxy-α-methyl-γ-butyrolactone.

In the case of KrF lithography, even in the case of using a structure unit derived from hydroxystyrene such as p-hydroxystyrene and m-hydroxystyrene, as one of components of the resin, a resist composition having sufficient transparency can be obtained. For obtaining such copolymerization resins, the corresponding acrylic or methacrylic ester monomer can be radical-polymerized with acetoxystyrene and styrene, and then the acetoxy group in the structure unit derived from acetoxystyrene can be de-acetylated with an acid.

The resin containing a structural unit derived from 2-norbornene shows strong structure because the alicyclic group is directly present on its main chain and shows a property that dry etching resistance is excellent. The structural unit derived from 2-norbornene can be introduced into the main chain by radical polymerization using, for example, an aliphatic unsaturated dicarboxylic anhydride such as maleic anhydride and itaconic anhydride together in addition to corresponding 2-norbornene. The structural unit derived from 2-norbornene is formed by opening of its double bond, and can be represented by the above-mentioned formula (XII). The structural unit derived from maleic anhydride and from itaconic anhydride which are the structural unit derived from aliphatic unsaturated dicarboxylic anhydrides are formed by opening of their double bonds, and can be represented by the above-mentioned formula (XIII) and the formula (XIV), respectively.

In $R^5$ and $R^6$, examples of the C1-C3 alkyl group include a methyl, ethyl, and n-propyl group, and examples of the C1-C3 hydroxyalkyl group include a hydroxymethyl and 2-hydroxyethyl group.

In $R^5$ and $R^6$, the —COOU group is an ester formed from the carboxyl group, and as the alcohol residue corresponding to U, for example, an optionally substituted C1-C8 alkyl group, 2-oxooxolan-3-yl group, 2-oxooxolan-4-yl and the like are listed, and as the substituent on the C1-C8 alkyl group, a hydroxyl group, an alicyclic hydrocarbon residue and the like are listed.

Specific examples of the monomer used to give the structural unit represented by the above-mentioned formula (XII) may include 2-norbornene, 2-hydroxy-5-norbornene, 5-norbornene-2-carboxylic acid, methyl 5-norbornene-2-carboxylate, 2-hydroxyethyl 5-norbornene-2-carboxylate, 5-norbornene-2-methanol and 5-norbornene-2,3-dicarboxylic anhydride.

When U in the —COOU group is the acid-labile group, the structural unit represented by the formula (XII) is a structural unit having the acid-labile group even if it has the norbornene structure. Examples of monomers giving structural unit having the acid-labile group include tert-butyl 5-norbornene-2-carboxylate, 1-cyclohexyl-1-methylethyl 5-norbornene-2-carboxylate, 1-methylcyclohexyl 5-norbornene-2-carboxylate, 2-methyl-2-adamantyl 5-norbornene-2-carboxylate, 2-ethyl-2-adamantyl 5-norbornene-2-carboxylate, 1-(4-methylcyclohexyl)-1-methylethyl 5-norbornene-2-carboxylate, 1-(4-hydroxylcyclohexyl)-1-methylethyl 5-norbornene-2-carboxylate, 1-methyl-1-(4- oxocyclohexyl)ethyl 5-norbornene-2-carboxylate, 1-(1-adamantyl)-1-methylethyl 5-norbornene-2-carboxylate, and the like.

The resin used in the present composition preferably contains the structural unit or units having the acid-labile group generally in a ratio of 10 to 80% by mole in all structural units of the resin though the ratio varies depending on the kind of radiation for patterning exposure, the kind of the acid-labile group, and the like.

When the structural units particularly derived from the 2-alkyl-2-adamantyl acrylate, the 2-alkyl-2-adamantyl methacrylate, the 1-(1-adamantyl)-1-alkylalkyl acrylate or the 1-(1-adamantyl)-1-alkylalkyl methacrylate are used as the structural unit having the acid-labile group, it is advantageous in dry-etching resistance of the resist that the ratio of the structural units is 15% by mole or more in all structural units of the resin.

When, in addition to structural units having the acid-labile group, other structural units having the acid-stable group are contained in the resin, it is preferable that the sum of these structural units is in the range of 20 to 90% by mole based on all structural units of the resin.

The resin used for the present composition can be produced by conducting polymerization reaction of the corresponding monomer or monomers. The resin can be also produced by conducting oligomerization of the corresponding monomer or monomers followed by polymerizing the oligomer obtained.

The polymerization reaction is usually carried out in the presence of a radical initiator.

The radical initiator is not limited and examples thereof include an azo compound such as 2,2'-azobisisobutyronitrile, 2,2'-azobis(2-methylbutyronitrile), 1,1'-azobis(cyclohexane-1-carbonitrile), 2,2'-azobis(2,4-dimethylvaleronitrile), 2,2'-azobis(2,4-dimethyl-4-methoxyvaleronitrile), dimethyl-2,2'-azobis(2-methylpropionate) and 2,2'-azobis(2-hydroxymethylpropionitrile); an organic hydroperoxide such as lauroyl peroxide, tert-butyl hydroperoxide, benzoyl peroxide, tert-butyl peroxybenzoate, cumene hydroperoxide, diisopropyl peroxydicarbonate, di-n-propyl peroxydicarbonate, tert-butyl peroxyneodecanoate, tert-butyl peroxypivalate and 3,5,5-trimethylhexanoyl peroxide; and an inorganic peroxide such as potassium peroxodisulfate, ammonium peroxodisulfate and hydrogen peroxide. Among them, the azo compound is preferable and 2,2'-azobisisobutyronitrile, 2,2'-azobis(2-methylbutyronitrile), 1,1'-azobis(cyclohexane-1-carbonitrile), 2,2'-azobis(2,4-dimethylvaleronitrile) and dimethyl-2,2'-azobis(2-methylpropionate) are more preferable, and 2,2'-azobisisobutyronitrile and 2,2'-azobis(2,4-dimethylvaleronitrile) are especially preferable.

These radical initiators may be used alone or in a form of a mixture of two or more kinds thereof. When the mixture of two or more kinds thereof is used, the mixed ratio is not particularly limited.

The amount of the radical initiator is preferably 1 to 20% by mole based on all monomer or oligomer molar amount.

The polymerization temperature is usually 0 to 150° C., and preferably 40 to 100° C.

The polymerization reaction is usually carried out in the presence of a solvent and it is preferred to use a solvent which is sufficient to dissolve the monomer, the radical initiator and the resin obtained. Examples thereof include a hydrocarbon solvent such as toluene; an ether solvent such as 1,4-dioxane and tetrahydrofuran; a ketone solvent such as methyl isobutyl ketone; an alcohol solvent such as isopropyl alcohol; a cyclic ester solvent such as γ-butyrolactone; a glycol ether ester ester solvent such as propylene glycol monomethyl ether acetate; and an acyclic ester solvent such as ethyl lactate. These solvents may be used alone and a mixture thereof may be used.

The amount of the solvent is not limited, and practically, it is preferably 1 to 5 parts by weight relative to 1 part of all monomers or oligomers.

When an alicyclic compound having an olefinic double bond and an aliphatic unsaturated dicarboxylic anhydride are used as monomers, it is preferable to use them in excess amount in view of a tendency that these are not easily polymerized.

After competition of the polymerization reaction, the resin produced can be isolated, for example, by adding a solvent in which the present resin is insoluble or poorly soluble to the reaction mixture obtained and filtering the precipitated resin. If necessary, the isolated resin may be purified, for example, by washing with a suitable solvent.

The present resist composition preferably includes 80 to 99.9% by weight of the resin component and 0.1 to 20% by weight of Salt (I) based on the total amount of the resin component and Salt (I).

In the present resist composition, performance deterioration caused by inactivation of acid which occurs due to post exposure delay can be diminished by adding an organic base compound, particularly a nitrogen-containing organic base compound as a quencher.

Specific examples of the nitrogen-containing organic base compound include an amine compound represented by the following formulae:

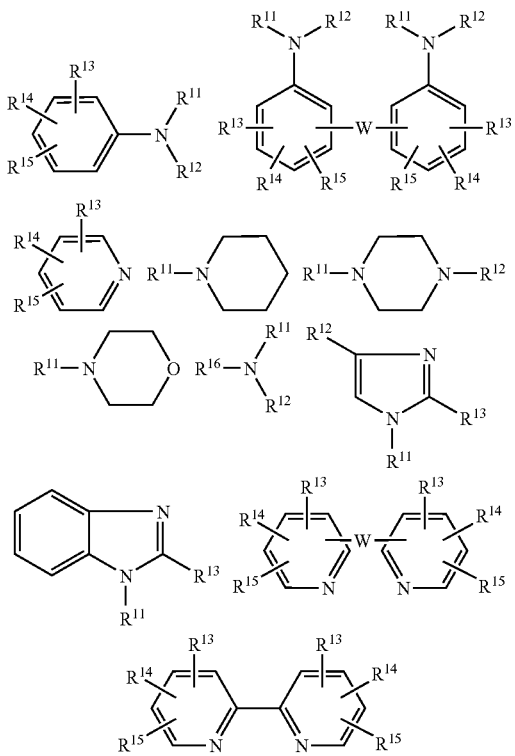

wherein $R^{11}$ and $R^{12}$ independently represent a hydrogen atom, an alkyl group, a cycloalkyl group or an aryl group, and the alkyl, cycloalkyl and aryl group may be substituted with at least one group selected from a hydroxyl group, an amino group which may be substituted with a C1-C4 alkyl group and a C1-C6 alkoxy group which may be substituted with a C1-C6 alkoxy group, $R^{13}$ and $R^{14}$ independently represent a hydrogen atom, an alkyl group, a cycloalkyl group, an aryl group or an alkoxy group, and the alkyl, cycloalkyl, aryl and alkoxy group may be substituted with at least one group selected from a hydroxyl group, an amino group which may be substituted with a C1-C4 alkyl group and a C1-C6 alkoxy group, or $R^{13}$ and $R^{14}$ bond together with the carbon atoms to which they bond to form an aromatic ring, $R^{15}$ represent a hydrogen atom, an alkyl group, a cycloalkyl group, an aryl group, an alkoxy group or a nitro group, and the alkyl, cycloalkyl, aryl and alkoxy group which may be substituted with at least one group selected from a hydroxyl group, an amino group which may be substituted with a C1-C4 alkyl group and a C1-C6 alkoxy group, $R^{16}$ represents an alkyl or cycloalkyl group, and the alkyl and cycloalkyl group may be substituted with at least one group selected from a hydroxyl group, an amino group which may be substituted with a C1-C4 alkyl group and a C1-C6 alkoxy group, and W represents —CO—, —NH—, —S—, —S—S—, an alkylene group of which at least one methylene group may be replaced with —O—, or an alkenylene group of which at least one methylene group may be replaced with —O—, and a quaternary ammonium hydroxide represented by the following formula:

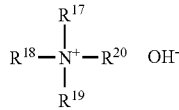

wherein $R^{17}$, $R^{18}$, $R^{19}$ and $R^{20}$ independently represent an alkyl group, a cycloalkyl group or an aryl group, and the alkyl, cycloalkyl and aryl group may be substituted with at least one group selected from a hydroxyl group, an amino group which may be substituted with a C1-C4 alkyl group and a C1-C6 alkoxy group.

The alkyl group in $R^{11}$, $R^{12}$, $R^{13}$, $R^{14}$, $R^{15}$, $R^{16}$, $R^{17}$, $R^{18}$, $R^{19}$ and $R^{20}$ preferably has about 1 to 10 carbon atoms, and more preferably has about 1 to 6 carbon atoms.

Examples of the amino group which may be substituted with the C1-C4 alkyl group include an amino, methylamino, ethylamino, n-butylamino, dimethylamino and diethylamino group. Examples of the C1-C6 alkoxy group which may be substituted with the C1-C6 alkoxy group include a methoxy, ethoxy, n-propoxy, isopropoxy, n-butoxy, tert-butoxy, n-pentyloxy, n-hexyloxy and 2-methoxyethoxy group.

Specific examples of the alkyl group which may be substituted with at least one group selected from a hydroxyl group, an amino group which may be substituted with a C1-C4 alkyl group, and a C1-C6 alkoxy group which may be substituted with a C1-C6 alkoxy group include a methyl, ethyl, n-propyl, isopropyl, n-butyl, tert-butyl, n-pentyl, n-hexyl, n-octyl, n-nonyl, n-decyl, 2-(2-methoxyethoxy)ethyl, 2-hydroxyethyl, 2-hydroxypropyl, 2-aminoethyl, 4-aminobutyl and 6-aminohexyl group.

The cycloalkyl group in $R^{11}$, $R^{12}$, $R^{13}$, $R^{14}$, $R^{15}$, $R^{16}$, $R^{17}$, $R^{18}$, $R^{19}$ and $R^{20}$ preferably has about 5 to 10 carbon atoms. Specific examples of the cycloalkyl group which may be substituted with at least one group selected from a hydroxyl group, an amino group which may be substituted with a C1-C4 alkyl group and a C1-C6 alkoxy group include a cyclopentyl, cyclohexyl, cycloheptyl and cyclooctyl group.

The aryl group in $R^{11}$, $R^{12}$, $R^{13}$, $R^{14}$, $R^{15}$, $R^{17}$, $R^{18}$, $R^{19}$ and $R^{20}$ preferably has about 6 to 10 carbon atoms. Specific examples of the aryl group which may be substituted with at least one group selected from a hydroxyl group, an amino group which may be substituted with a C1-C4 alkyl group and a C1-C6 alkoxy group include a phenyl and naphthyl group.

The alkoxy group in $R^{13}$, $R^{14}$ and $R^{15}$ preferably has about 1 to 6 carbon atoms and specific examples thereof include a methoxy, ethoxy, n-propoxy, isopropoxy, n-butoxy, tert-butoxy, n-pentyloxy and n-hexyloxy group.

The alkylene and alkenylene groups in W preferably have 2 to 6 carbon atoms. Specific examples of the alkylene group include an ethylene, trimethylene, tetramethylene, methylenedioxy and ethylene-1,2-dioxy group, and specific examples of the alkenylene group include an ethane-1,2-diyl, 1-propene-1,3-diyl and 2-butene-1,4-diyl group.

Specific examples of the amine compound include n-hexylamine, n-heptylamine, n-octylamine, n-nonylamine, n-decylamine, aniline, 2-methylaniline, 3-methylaniline, 4-methylaniline, 4-nitroaniline, 1-naphthylamine, 2-naphthylamine, ethylenediamine, tetramethylenediamine, hexamethylenediamine, 4,4'-diamino-1,2-diphenylethane, 4,4'-diamino-3,3'-dimethyldiphenylmethane, 4,4'-diamino-3,3'-diethyldiphenylmethane, dibutylamine, dipentylamine, dihexylamine, diheptylamine, dioctylamine, dinonylamine, didecylamine, N-methylaniline, piperidine, diphenylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethyldipentylamine, ethyldihexylamine, ethyldiheptylamine, ethyldioctylamine, ethyldinonylamine, ethyldidecyamine, dicyclohexylmethylamine, tris[2-(2-methoxyethoxy)ethyl]amine, triisopropanolamine, N,N-dimethylaniline, 2,6-diisopropylaniline, imidazole, benzimidazole, pyridine, 4-methylpyridine, 4-methylimidazole, bipyridine, 2,2'-dipyridylamine, di-2-pyridyl ketone, 1,2-di(2-pyridyl)ethane, 1,2-di(4-pyridyl)ethane, 1,3-di(4-pyridyl)propane, 1,2-bis(2-pyridyl)ethylene, 1,2-bis(4-pyridyl)ethylene, 1,2-bis(4-pyridyloxy)ethane, 4,4'-dipyridyl sulfide, 4,4'-dipyridyl disulfide, 1,2-bis(4-pyridyl)ethylene, 2,2'-dipicolylamine and 3,3'-dipicolylamine.

Examples of the quaternary ammonium hydroxide include tetramethylammonium hydroxide, tetrabutylammonium hydroxide, tetrahexylammonium hydroxide, tetraoctylammonium hydroxide, phenyltrimethylammonium hydroxide, (3-trifluoromethylphenyl)trimethylammonium hydroxide and (2-hydroxyethyl)trimethylammonium hydroxide (so-called "choline").

A hindered amine compound having a piperidine skeleton as disclosed in JP 11-52575 A1 can be also used as the quencher.

In the point of forming patterns having higher resolution, the quaternary ammonium hydroxide is preferably used as the quencher.

When the basic compound is used as the quencher, the present resist composition preferably includes 0.01 to 1% by weight of the basic compound based on the total amount of the resin component and Salt (I).

The present resist composition can contain, if necessary, a small amount of various additives such as a sensitizer, a solution suppressing agent, other polymers, a surfactant, a stabilizer and a dye as long as the effect of the present invention is not prevented.

The present resist composition is usually in the form of a resist liquid composition in which the above-mentioned ingredients are dissolved in a solvent and the resist liquid composition is applied onto a substrate such as a silicon wafer by a conventional process such as spin coating. The solvent used is sufficient to dissolve the above-mentioned ingredients, have an adequate drying rate, and give a uniform and smooth coat after evaporation of the solvent. Solvents generally used in the art can be used.

Examples of the solvent include a glycol ether ester such as ethyl cellosolve acetate, methyl cellosolve acetate and propylene glycol monomethyl ether acetate; an acyclic ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone. These solvents may be used alone and two or more thereof may be mixed to use.

A resist film applied onto the substrate and then dried is subjected to exposure for patterning, then heat-treated to facilitate a deblocking reaction, and thereafter developed with an alkali developer. The alkali developer used may be any one of various alkaline aqueous solution used in the art. Generally, an aqueous solution of tetramethylammonium hydroxide or (2-hydroxyethyl)trimethylammonium hydroxide (commonly known as "choline") is often used.

It should be construed that embodiments disclosed here are examples in all aspects and not restrictive. It is intended that the scope of the present invention is determined not by the above descriptions but by appended Claims, and includes all variations of the equivalent meanings and ranges to the Claims.

The present invention will be described more specifically by Examples, which are not construed to limit the scope of the present invention. The "%" and "part(s)" used to represent the content of any component and the amount of any material to be used in the following Examples are on a weight basis unless otherwise specifically noted. The weight-average molecular weight of any material in the following Examples is a value found by gel permeation chromatography [HLC-8120GPC Type, Column (Total 3 Columns): TSKgel Multipore HXL-M manufactured by TOSOH CORPORATION, Solvent: tetrahydrofuran] using polystyrene as a standard reference material.

Structures of salts obtained were determined by NMR (GX-270 Type or EX-270 Type, manufactured by JEOL LTD.) and mass spectrometry (Liquid Chromatography: 1100 Type manufactured by AGILENT TECHNOLOGIES LTD., Mass Spectrometry: LC/MSD Type or LC/MSD TOF Type manufactured by AGILENT TECHNOLOGIES LTD.).

Salt Synthesis Example 1

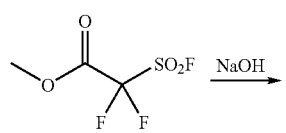

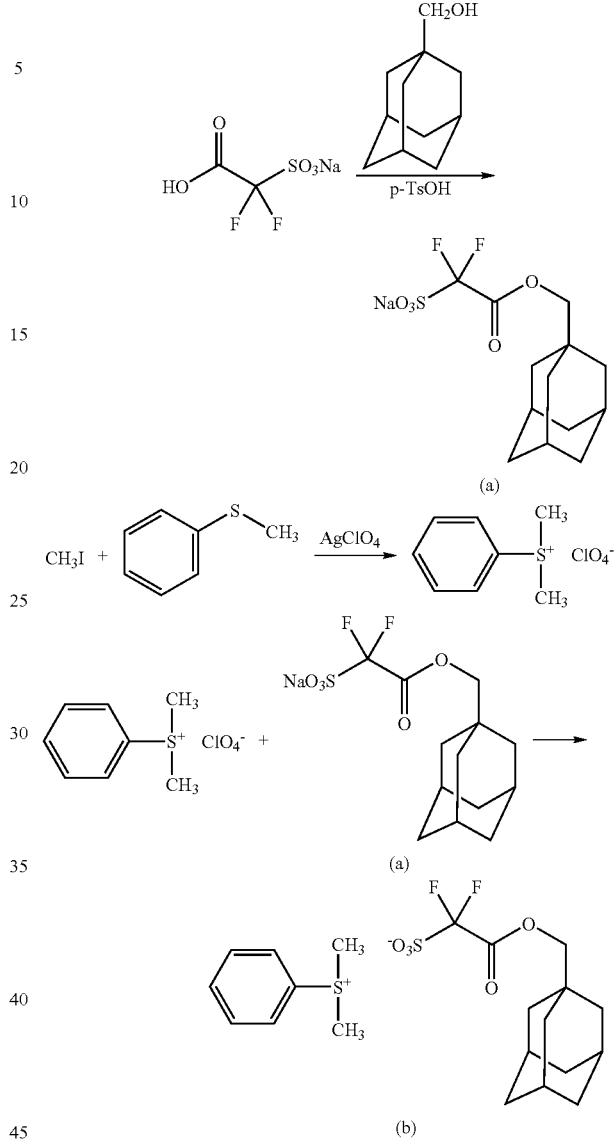

(1) 460 Parts of 30% aqueous sodium hydroxide solution was added dropwise into a mixture of 200 parts of methyl difluoro (fluorosulfonyl)acetate and 300 parts of ion-exchanged water in an ice bath. The resultant mixture was refluxed at 100° C. for 2.5 hours and cooled. The mixture was neutralized with 175 parts of conc. hydrochloric acid. The resultant mixture was concentrated to obtain 328.2 parts of sodium salt of difluorosulfoacetic acid (in which inorganic salts were contained, purity: 62.8%).

(2) 75.1 Parts of p-toluenesulfonic acid was added to a mixture of 123.3 parts of sodium salt of difluorosulfoacetic acid obtained in the above (1), 65.7 parts of 1-adamantanemethanol and 600 parts of dichloroethane, and the resultant mixture was heated and refluxed for 12 hours. The mixture was concentrated to remove dichloroethane and 400 parts of tert-butyl methyl ether was added to the residue obtained. The mixture obtained was stirred and filtrated to obtain the solid. To the solid, 400 parts of acetonitrile was added and the resultant mixture was stirred and filtrated to obtain the solid. To the solid, 400 parts of acetonitrile was added and the resultant mixture was stirred and filtrated. The filtrates obtained were mixed and the solution obtained was concentrated to obtain 99.5 parts of the salt represented by the above-mentioned formula (a).

$^1$H-NMR (dimethylsulfoxide-$d_6$, Internal standard: tetramethylsilane): δ (ppm) 1.51 (d, 6H), 1.62 (dd, 6H), 1.92 (s, 3H), 3.80 (s, 2H)

(3) 5.0 Parts of thioanisole was dissolved in 15.0 parts of acetonitrile. To the solution obtained, 8.35 parts of silver (I) perchlorate was added and a solution of 5.71 parts of methyl iodide and 11.4 parts of acetonitrile was further added thereto to stir for 24 hours. After removing the precipitated solid by filtration, the filtrate obtained was concentrated to remove acetonitrile. To the concentrated liquid, 36.8 parts of tert-butyl methyl ether was added and stirred. The resultant mixture was filtrated to obtain 8.22 parts of dimethylphenylsulfonium perchlorate in the form of white solid.

$^1$H-NMR (dimethylsulfoxide-$d_6$, Internal standard: tetramethylsilane): δ (ppm) 3.25 (s, 6H), 7.67-7.80 (m, 3H), 8.03-8.08 (m, 2H)

(4) 5.98 Parts of the salt represented by the formula (a), which was obtained in the above-mentioned (2), was mixed with 35.9 parts of chloroform. To the mixture obtained, 4.23 parts of dimethylphenylsulfonium perchlorate obtained in the above-mentioned (3) and 12.7 parts of ion-exchanged water were added to stir for 4 hours. The resultant mixture was separated to obtain an organic layer and an aqueous layer. The aqueous layer was extracted with 23.9 parts of chloroform to obtain a chloroform layer. The organic layer and the chloroform layer were mixed and the solution obtained was washed with ion-exchanged water and concentrated. To the concentrated liquid obtained, 31.8 parts of tert-butyl methyl ether was added and stirred. The resultant mixture was filtrated to obtain 5.38 parts of the salt represented by the above-mentioned formula (b) in the form of white solid, which is called as B1.

$^1$H-NMR (dimethylsulfoxide-$d_6$, Internal standard: tetramethylsilane): δ (ppm) 1.51 (d, 6H), 1.62 (dd, 6H), 1.92 (s, 3H), 3.26 (s, 6H), 3.80 (s, 2H), 7.68-7.80 (m, 3H), 8.03-8.06 (m, 2H)

MS (ESI(+) Spectrum): M$^+$ 139.0 ($C_8H_{11}S^+$=139.06)

MS (ESI(−) Spectrum): M$^-$ 323.0 ($C_{13}H_{17}F_2O_5S^-$= 323.08)

Salt Synthesis Example 2

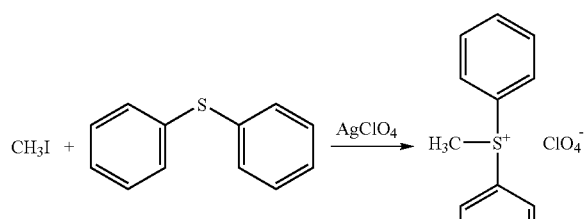

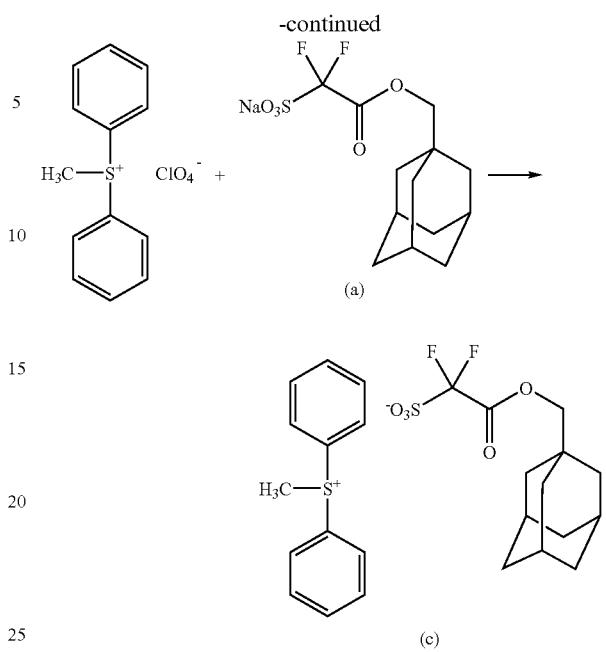

(1) 6.56 Parts of diphenyl sulfide was dissolved in 19.7 parts of acetonitrile. To the solution obtained, 7.30 parts of silver (I) perchlorate was added and a solution of 5.00 parts of methyl iodide and 10.0 parts of acetonitrile was further added thereto to stir for 24 hours. After removing the precipitated solid by filtration, the filtrate was concentrated to remove acetonitrile. To the concentrated liquid, 39.2 parts of tert-butyl methyl ether was added and stirred. The resultant mixture was filtrated to obtain 9.38 parts of methyldiphenylsulfonium perchlorate in the form of white solid.

$^1$H-NMR (dimethylsulfoxide-$d_6$, Internal standard: tetramethylsilane): δ (ppm) 3.81 (s, 3H), 7.67-7.79 (m, 6H), 8.01-8.04 (m, 4H)

(2) 8.29 Parts of the salt represented by the formula (a), which was synthesized in a similar manner to the method described in the above-mentioned Salt Synthesis Example 1 (2), was mixed with 49.7 parts of chloroform. To the mixture obtained, a mixture of 9.38 parts of methyldiphenylsulfonium perchlorate obtained in the above-mentioned (1) and 28.14 parts of ion-exchanged water was added to stir for 15 hours. The resultant mixture was separated to obtain an organic layer and an aqueous layer. The aqueous layer was extracted with 33.1 parts of chloroform to obtain a chloroform layer. The organic layer and the chloroform layer were mixed and the solution obtained was washed with ion-exchanged water and concentrated. To the concentrated liquid obtained, 33.8 parts of tert-butyl methyl ether was added and stirred. The supernatant liquid was removed from the resultant mixture by decantation to obtain 7.81 parts of the salt represented by the above-mentioned formula (c) in the form of colorless liquid, which is called as B2.

$^1$H-NMR (dimethylsulfoxide-$d_6$, Internal standard: tetramethylsilane): δ (ppm) 1.50 (d, 6H), 1.61 (dd, 6H), 1.91 (s, 3H), 3.80 (s, 2H), 3.82 (s, 3H), 7.67-7.79 (m, 6H), 8.02-8.05 (m, 4H)

MS (ESI(+) Spectrum): M⁺ 201.0 ($C_{13}H_{13}S^+$=201.07)

MS (ESI(−) Spectrum): M⁻ 323.0 ($C_{13}H_{17}F_2O_5S^-$=323.08)

Salt Synthesis Example 3

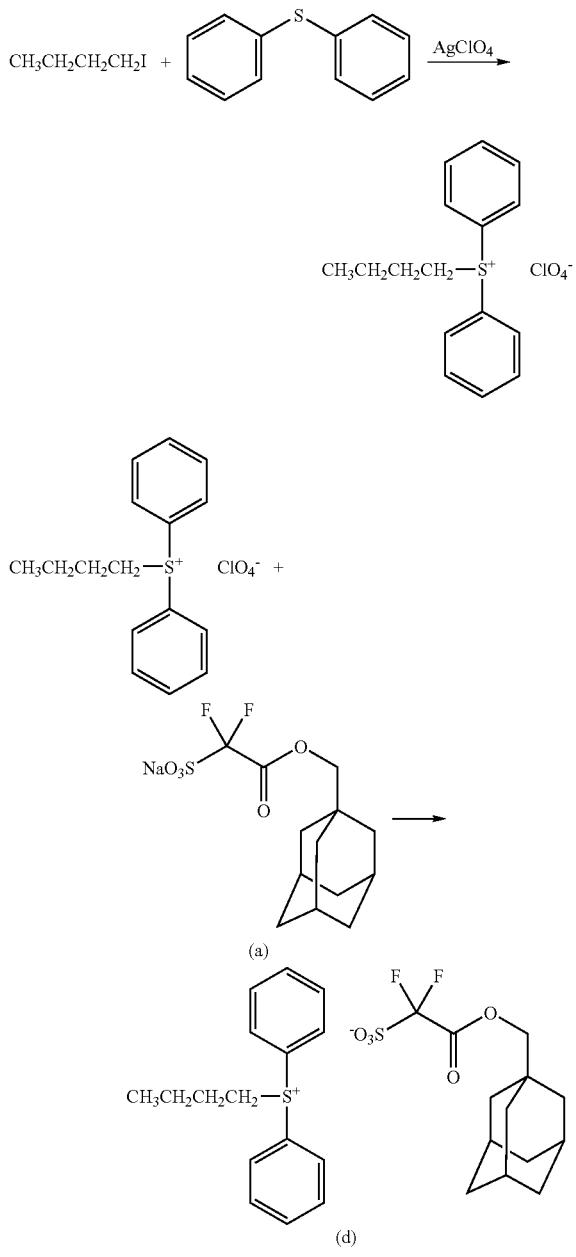

(1) 26.5 Parts of diphenyl sulfide was dissolved in 79.4 parts of acetonitrile. To the solution obtained, 29.5 parts of silver (I) perchlorate was added and a solution of 26.2 parts of n-butyl iodide and 52.3 parts of acetonitrile was further added thereto to stir for 24 hours. After removing the precipitated solid by filtration, the filtrate was concentrated to remove acetonitrile. To the concentrated liquid obtained, 135.9 parts of tert-butyl methyl ether was added and stirred. The resultant mixture was filtrated to obtain the residue. To the residue obtained, 101.7 parts of tert-butyl methyl ether was added and stirred. The resultant mixture was filtrated to obtain 14.8 parts of n-butyl-diphenylsulfonium perchlorate in the form of white solid.

¹H-NMR (dimethylsulfoxide-$d_6$, Internal standard: tetramethylsilane): δ (ppm) 0.88 (t, 3H), 1.41-1.49 (m, 2H), 1.52-1.64 (m, 2H), 4.31 (t, 2H), 7.69-7.82 (m, 6H), 8.08 (d, 4H)

(2) 5.00 Parts of the salt represented by the formula (a), which was synthesized in a similar manner to the method described in the above-mentioned Salt Synthesis Example 1 (2), was mixed with 50.0 parts of chloroform. To the mixture obtained, a mixture of 13.94 parts of n-butyldiphenylsulfonium perchlorate obtained in the above-mentioned (1) and 41.82 parts of ion-exchanged water was added to stir for 15 hours. The resultant mixture was separated to obtain an organic layer and an aqueous layer. The aqueous layer was extracted with 10.0 parts of chloroform to obtain a chloroform layer. The organic layer and the chloroform layer were mixed and the solution obtained was washed with ion-exchanged water and concentrated. To the concentrated liquid obtained, 37.6 parts of tert-butyl methyl ether was added and stirred. The resultant mixture was filtrated to obtain the residue. The residue was mixed with 16.8 parts of ethyl acetate and the resultant mixture was stirred and filtrated to obtain 2.89 parts of the salt represented by the above-mentioned formula (d) in the form of white solid, which is called as B3.

¹H-NMR (dimethylsulfoxide-$d_6$, Internal standard: tetramethylsilane): δ (ppm) 0.88 (t, 3H), 1.42-1.67 (m, 16H), 1.91 (s, 3H), 3.80 (s, 2H), 4.33 (t, 2H), 7.71-7.83 (m, 6H), 8.09 (d, 4H)

MS (ESI(+) Spectrum): M⁺ 243.11 ($C_{16}H_{19}S^+$=243.12)

MS (ESI(−) Spectrum): M⁻ 323.10 ($C_{13}H_{17}F_2O_5S^-$=323.08)

Salt Synthesis Example 4

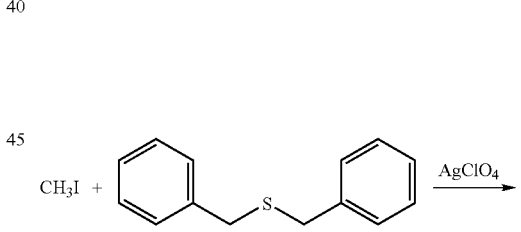

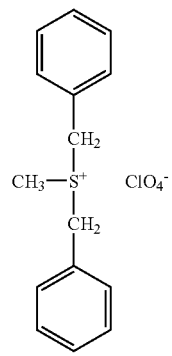

-continued

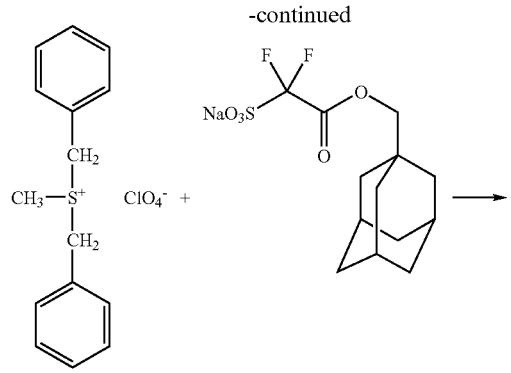

(a)

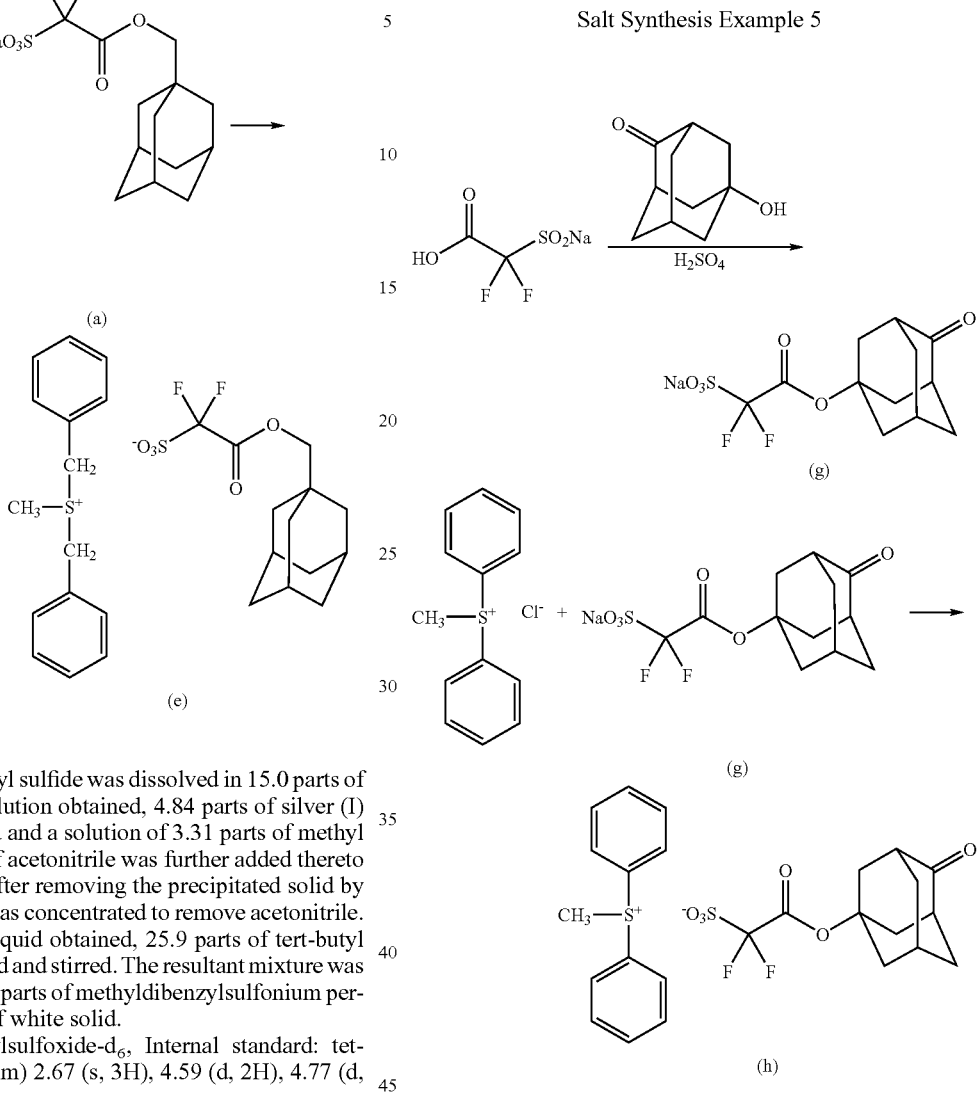

MS (ESI(+) Spectrum): M+ 229.2 (C$_{15}$H$_{17}$S+=229.10)
MS (ESI(−) Spectrum): M− 323.0 (C$_{13}$H$_{17}$F$_2$O$_5$S−= 323.08)

Salt Synthesis Example 5

(1) 5.0 Parts of dibenzyl sulfide was dissolved in 15.0 parts of acetonitrile. To the solution obtained, 4.84 parts of silver (I) perchlorate was added and a solution of 3.31 parts of methyl iodide and 6.6 parts of acetonitrile was further added thereto to stir for 24 hours. After removing the precipitated solid by filtration, the filtrate was concentrated to remove acetonitrile. To the concentrated liquid obtained, 25.9 parts of tert-butyl methyl ether was added and stirred. The resultant mixture was filtrated to obtain 5.89 parts of methyldibenzylsulfonium perchlorate in the form of white solid.

$^1$H-NMR (dimethylsulfoxide-d$_6$, Internal standard: tetramethylsilane): δ (ppm) 2.67 (s, 3H), 4.59 (d, 2H), 4.77 (d, 2H), 7.45 (s, 10H)

(2) 3.11 Parts of the salt represented by the formula (a), which was synthesized in a similar manner to the method described in the above-mentioned Salt Synthesis Example 1 (2), was mixed with 31.1 parts of chloroform. To the mixture obtained, a mixture of 3.18 parts of methyldibenzylsulfonium perchlorate obtained in the above-mentioned (1) and 9.54 parts of ion-exchanged water was added to stir for 4 hours. The resultant mixture was separated to obtain an organic layer and an aqueous layer. The aqueous layer was extracted with 15.5 parts of chloroform to obtain a chloroform layer. The organic layer and the chloroform layer were mixed and the solution obtained was washed with ion-exchanged water and concentrated. To the concentrated liquid obtained, 19.4 parts of tert-butyl methyl ether was added and stirred. The resultant mixture was filtrated to obtain 3.65 parts of the salt represented by the above-mentioned formula (e) in the form of white solid, which is called as B4.

$^1$H-NMR (dimethylsulfoxide-d$_6$, Internal standard: tetramethylsilane): δ (ppm) 1.50 (d, 6H), 1.62 (dd, 6H), 1.92 (s, 3H), 2.67 (s, 3H), 3.80 (s, 2H), 4.59 (d, 2H), 4.77 (d, 2H), 7.45 (s, 10H)

(1) 5.0 Parts of sodium salt of difluorosulfoacetic acid (purity: 62.8%) synthesized in a similar manner to the method described in the above-mentioned Salt Synthesis Example 1 (1), 2.6 parts of 4-oxo-1-adamantanol and 100 parts of ethylbenzene were mixed. To the resultant mixture, 0.8 part of conc. sulfuric acid was added and the mixture obtained was refluxed for 30 hours. The reaction mixture was cooled and then, filtrated to obtain the solid. The solid obtained was washed with tert-butyl methyl ether to obtain 5.5 parts of the salt represented by the above-mentioned formula (g) (hereinafter, simply referred to as the salt (g)). The purity thereof was analyzed by $^1$H-NMR, and as a result, the purity was 49.1%.

$^1$H-NMR (dimethylsulfoxide-d$_6$, Internal standard: tetramethylsilane): δ (ppm) 1.84 (d, 2H), 2.00 (d, 2H), 2.29-2.32 (m, 7H), 2.54 (s, 2H)

(2) 42.0 Parts of aqueous methyldiphenylsulfonium chloride solution (content: 5.0%) was added to a mixture of 5.0 parts of the salt (g) obtained in above-mentioned (1) and 50.0 parts of chloroform. The resultant mixture was stirred for 15 hours and separated to obtain an organic layer and an aqueous layer.

The aqueous layer was extracted with 25.0 parts of chloroform to obtain a chloroform layer. The organic layer and the chloroform layer were mixed. The organic solution obtained was repeated to wash with ion-exchanged water until the aqueous layer obtained was neutralized. The organic layer obtained was concentrated. The concentrated liquid obtained was mixed with 29.6 parts of tert-butyl methyl ether. The resultant mixture was stirred. The residue was obtained by decantation and 16.6 parts of ethyl acetate was added to the residue. The resultant mixture was stirred. By decantation, 1.6 parts of the salt represented by the above-mentioned formula (h) in the form of pale yellow liquid was obtained, which is called as B5.

$^1$H-NMR (dimethylsulfoxide-$d_6$, Internal standard: tetramethylsilane): δ (ppm) 1.82 (d, 2H), 1.99 (d, 2H), 2.21-2.35 (m, 7H), 2.52 (s, 2H), 3.81 (s, 3H), 7.67-7.79 (m, 6H), 8.01-8.06 (m, 4H)

Salt Synthesis Example 6

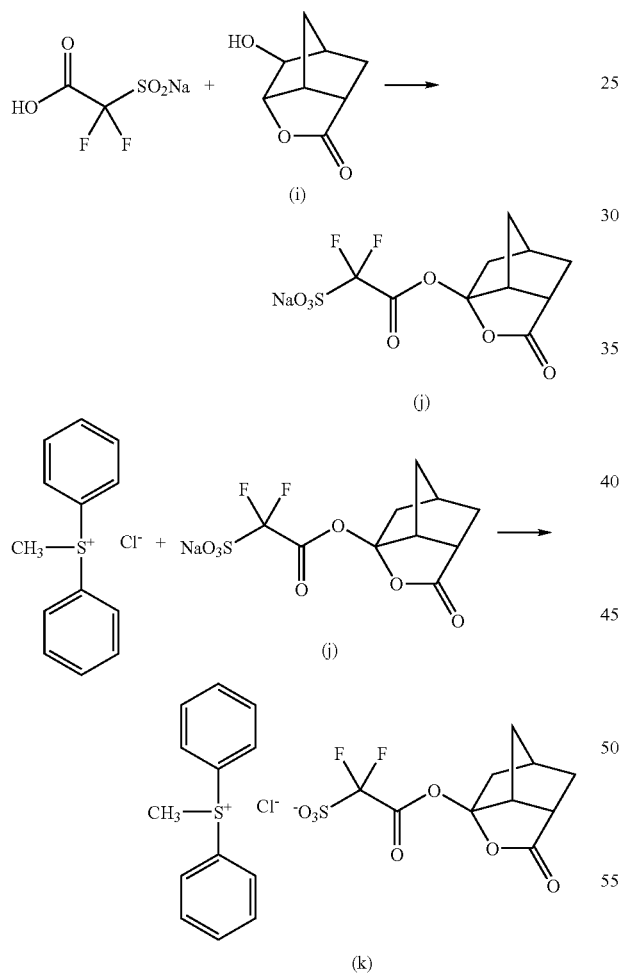

(1) 30.0 Parts of sodium salt of difluorosulfoacetic acid (purity: 62.8%) synthesized in a similar manner to the method described in the above-mentioned Salt Synthesis Example 1 (1), 14.7 parts of the compound represented by the above-mentioned formula (i) and 300 parts of toluene were mixed. To the resultant mixture, 18.1 part of p-toluenesulfonic acid was added and the mixture obtained was refluxed for 12 hours. The reaction mixture was filtrated to obtain the solid. The solid obtained was mixed with 100 parts of acetonitrile and the resultant mixture was stirred. The mixture was filtrated and the filtrate obtained was concentrated to obtain 26.7 parts of the salt represented by the above-mentioned formula (j) (hereinafter, simply referred to as the salt (j)).

$^1$H-NMR (dimethylsulfoxide-$d_6$, Internal standard: tetramethylsilane): δ (ppm) 1.57-1.67 (m, 2H), 1.91-2.06 (m, 2H), 2.53 (dd, 1H), 3.21 (td, 1H), 4.51 (d, 1H), 4.62 (s, 1H)

(2) 43.5 Parts of aqueous methyldiphenylsulfonium chloride solution (content: 5.0%) was added to a mixture of 2.5 parts of the salt (j) obtained in above-mentioned (1) and 50.0 parts of chloroform. The resultant mixture was stirred for 15 hours and separated to obtain an organic layer and an aqueous layer. The aqueous layer was extracted with 25.0 parts of chloroform to obtain a chloroform layer. The organic layer and the chloroform layer were mixed. The organic solution obtained was repeated to wash with ion-exchanged water until the aqueous layer obtained was neutralized. The organic layer obtained was concentrated. The concentrated liquid obtained was mixed with 24.2 parts of tert-butyl methyl ether. The resultant mixture was stirred. The residue was obtained by decantation and 11.9 parts of ethyl acetate was added to the residue. The resultant mixture was stirred. By decantation, 1.1 parts of the salt represented by the above-mentioned formula (k) in the form of pale yellow liquid was obtained, which is called as B6.

$^1$H-NMR (dimethylsulfoxide-$d_6$, Internal standard: tetramethylsilane): δ (ppm) 1.55-1.66 (m, 2H), 1.89-2.07 (m, 2H), 2.52 (dd, 1H), 3.21 (td, 1H), 3.81 (s, 3H), 4.49 (d, 1H), 4.61 (s, 1H), 7.67-7.79 (m, 6H), 8.01-8.05 (m, 4H)

Comparative Salt Synthesis Example 1

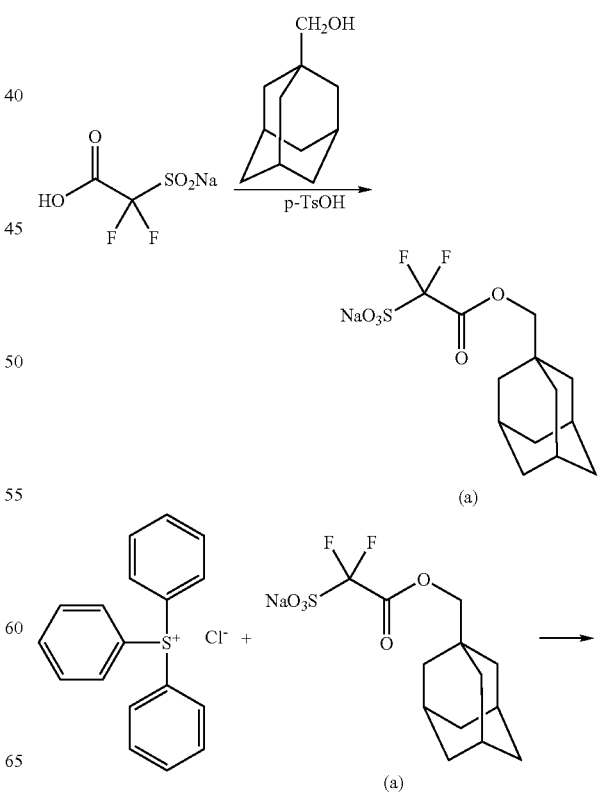

-continued

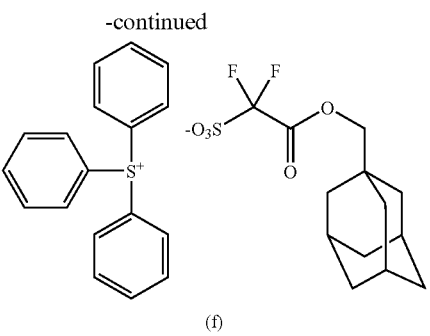

(f)

(1) 24.0 Parts of p-toluenesulfonic acid was added to a mixture of 39.4 Parts of sodium salt of difluorosulfoacetic acid (purity: 63.5%), 21.0 parts of 1-adamantanemethanol and 200 parts of dichloroethane, and the resultant mixture was heated and refluxed for 7 hours. The mixture was concentrated to remove dichloroethane and 250 parts of tert-butyl methyl ether was added to the residue obtained. The mixture obtained was stirred and filtrated to obtain the solid. To the solid, 250 parts of acetonitrile was added and the resultant mixture was stirred and filtrated. The filtrate obtained was concentrated to obtain 32.8 parts of the salt represented by the above-mentioned formula (a).

(2) 32.8 Parts of the salt obtained in the above-mentioned (1) was dissolved in 100 parts of ion-exchanged water. To the solution obtained, a mixture of 28.3 parts of triphenylsulfonium chloride and 140 parts of methanol was added to stir for 15 hours. The resultant mixture was concentrated. The residue obtained was extracted twice with 200 parts of chloroform. The organic layers obtained were mixed and washed with ion-exchanged water and then, concentrated. To the concentrated liquid obtained, 300 parts of tert-butyl methyl ether was added and stirred. The resultant mixture was filtrated and the solid obtained was dried to obtain 39.7 parts of the salt represented by the above-mentioned formula (f) in the form of white solid, which is called as C1.

$^1$H-NMR (dimethylsulfoxide-$d_6$, Internal standard: tetramethylsilane): δ (ppm) 1.52 (d, 6H), 1.63 (dd, 6H), 1.93 (s, 3H), 3.81 (s, 2H), 7.76-7.90 (m, 15H)

MS (ESI(+) Spectrum): M$^+$ 263.2 ($C_{18}H_{15}S^+$=263.09)

MS (ESI(−) Spectrum): M$^-$ 323.0 ($C_{13}H_{17}F_2O_5S^-$=323.08)

Comparative Salt Synthesis Example 2

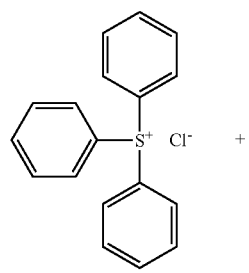

-continued

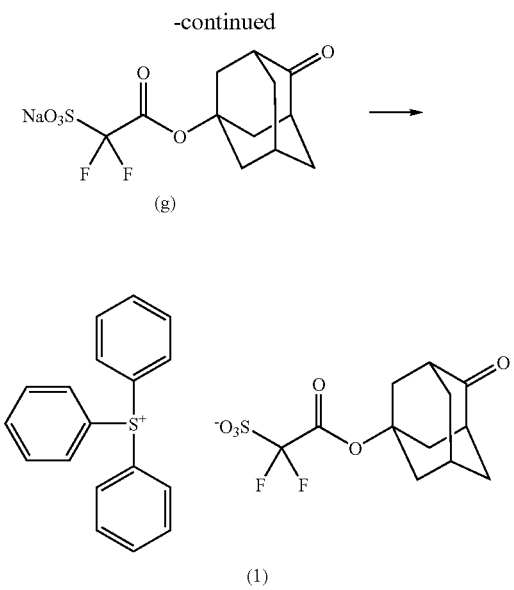

A mixture of 16 parts of acetonitrile and 16 parts of ion-exchanged water was added to 5.4 parts of the salt (g) (purity: 35.6%) synthesized in a similar manner to the method described in the above-mentioned Salt Synthesis Example 5 (1). To the resultant mixture, a solution of 1.7 parts of triphenylsulfonium chloride, 5 parts of acetonitrile and 5 parts of ion-exchanged water was added. The mixture obtained was stirred for 15 hours and concentrated. The residue obtained was extracted with 142 parts of chloroform and the organic layer obtained was repeated to wash until the aqueous layer obtained was neutralized. The organic layer obtained was concentrated. The concentrated liquid obtained was mixed with 24 parts of tert-butyl methyl ether. The resultant mixture was stirred and filtrated to obtain 1.7 parts of the salt represented by the above-mentioned formula (1) in the form of white solid, which is called as C2.

$^1$H-NMR (dimethylsulfoxide-$d_6$, Internal standard: tetramethylsilane): δ (ppm) 1.83 (d, 2H, J=12.7 Hz), 2.00 (d, 2H, J=12.0 Hz), 2.29-2.32 (m, 7H), 2.53 (s, 2H), 7.75-7.91 (m, 15H)

MS (ESI(+) Spectrum): M$^+$ 263.2 ($C_{18}H_{15}S^+$=263.09)

MS (ESI(−) Spectrum): M$^-$ 323.0 ($C_{12}H_{13}F_2O_6S^-$=323.04)

Comparative Salt Synthesis Example 3

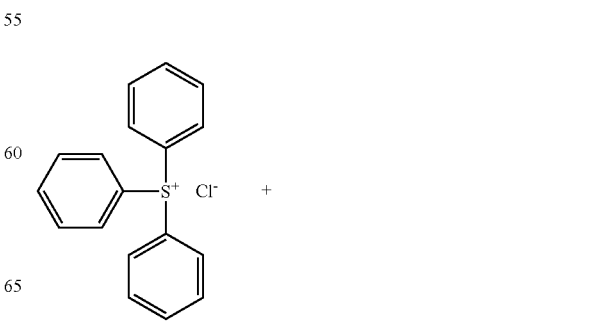

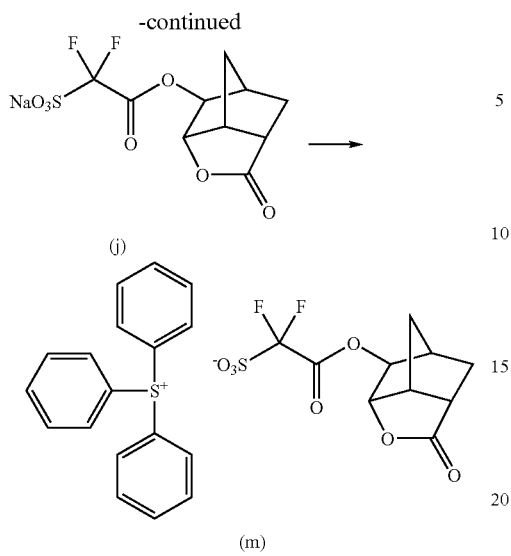

(j)

(m)

26.7 Parts of the salt (j) synthesized in a similar manner to the method described in the above-mentioned Salt Synthesis Example 6(1) was dissolved in 267 parts of acetonitrile. To the solution obtained, 23.9 parts of triphenylsulfonium chloride and 239 parts of ion-exchanged water were added. The mixture obtained was stirred for 15 hours and concentrated. The residue obtained was extracted twice with 260 parts of chloroform. The organic layers obtained were mixed and repeated to wash until the aqueous layer obtained was neutralized. The organic layer obtained was concentrated. The concentrated liquid obtained was mixed with 200 parts of tert-butyl methyl ether. The resultant mixture was stirred and filtrated to obtain 37.7 parts of the salt represented by the above-mentioned formula (m) in the form of pale yellow oil, which is called as C3.

$^1$H-NMR (dimethylsulfoxide-$d_6$, Internal standard: tetramethylsilane): δ (ppm) 1.57-1.67 (m, 2H), 1.91-2.06 (m, 2H), 2.53 (dd, 1H), 3.21 (td, 1H), 4.51 (d, 1H), 4.62 (s, 1H), 7.76-7.91 (m, 15H)

MS (ESI(+) Spectrum): $M^+$ 263.2 ($C_{18}H_{15}S^+$=263.09)

MS (ESI(−) Spectrum): $M^-$ 311.0 ($C_{10}H_9F_2O_7S^-$=311.00)

Resin Synthesis Example 1

2-Ethyl-2-adamantyl methacrylate, 3-hydroxy-1-adamantyl methacrylate and α-methacryloyloxy-γ-butyrolactone were dissolved in 2 times amount of methyl isobutyl ketone as much as the amount of all monomers to be used (monomer molar ratio; 2-ethyl-2-adamantyl methacrylate:3-hydroxy-1-adamantyl methacrylate:α-methacryloyloxy-γ-butyrolactone=5:2.5:2.5). To the solution, 2,2'-azobisisobutyronitrile was added as an initiator in a ratio of 2 mol % based on all monomer molar amount, and the resultant mixture was heated at 80° C. for about 8 hours. The reaction solution was poured into large amount of heptane to cause precipitation. The precipitate was isolated and washed twice with large amount of heptane for purification. As a result, copolymer having a weight-average molecular weight of about 9,200 was obtained. This copolymer had the following structural units. This is called as resin A1.

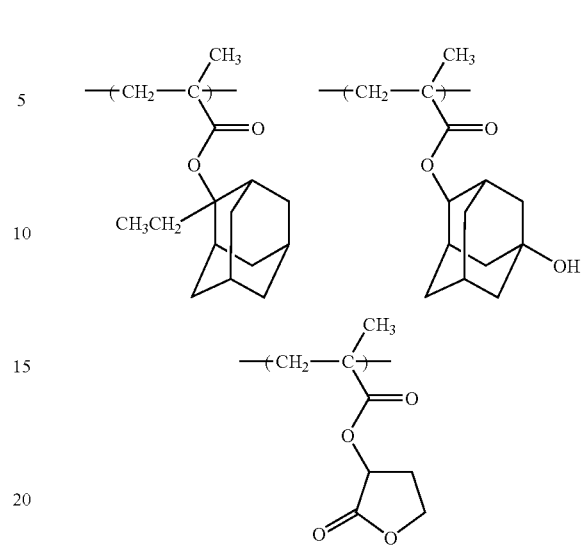

Examples 1 to 2 and Comparative Example 1

Resin

Resin A1

<Acid Generator>

Acid generator B2:

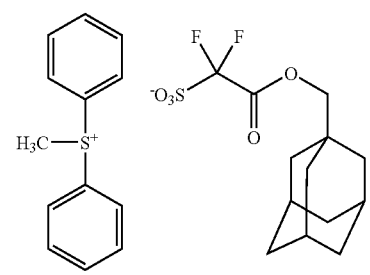

Acid generator B3:

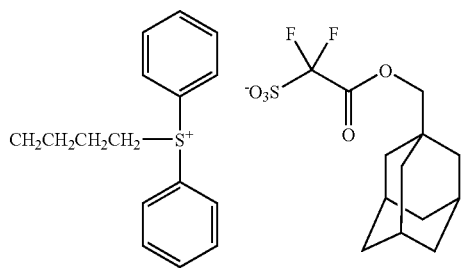

Acid generator C1:

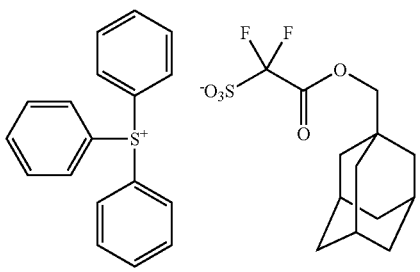

<Quencher>

Quencher Q1: 2,6-diisopropylaniline

<Solvent>

| Solvent Y1: | propylene glycol monomethyl ether acetate | 51.5 parts |
| --- | --- | --- |
| | 2-heptanone | 35.0 parts |
| | γ-butyrolactone | 3.5 parts |

The following components were mixed to give a solution, and the solution was further filtrated through a fluorine resin filter having a pore diameter of 0.2 μm, to prepare resist liquid.
Resin (kind and amount are described in Table 1)
Acid generator (kind and amount are described in Table 1)
Quencher (kind and amount are described in Table 1)
Solvent (kind and amount are described in Table 1)

TABLE 1

| Ex. No. | Resin (kind/amount (part)) | Acid generator (kind/amount (part)) | Quencher (kind/amount (part)) | Solvent |
| --- | --- | --- | --- | --- |
| Ex. 1 | A1/10 | B2/0.23 | Q1/0.0325 | Y1 |
| Ex. 2 | A1/10 | B3/0.25 | Q1/0.0325 | Y1 |
| Comp. Ex. 1 | A1/10 | C1/0.26 | Q1/0.0325 | Y1 |

Silicon wafers were each coated with "ARC-29A-8", which is an organic anti-reflective coating composition available from Nissan Chemical Industries, Ltd., and then baked under the conditions of 215° C. and 60 seconds, to form a 780 Å-thick organic anti-reflective coating. Each of the resist liquids prepared as above was spin-coated over the anti-reflective coating so that the thickness of the resulting film became 0.25 μm after drying. After application of each of the resist liquids, the silicon wafers thus coated with the respective resist liquids were each prebaked on a direct hotplate at a temperature of 130° C. for 60 seconds. Using an ArF excimer stepper ("NSR ArF" manufactured by Nikon Corporation, NA=0.55, ⅔ Annular), each wafer on which the respective resist film had been thus formed was exposed to a line and space pattern, while changing stepwise the exposure quantity.

After the exposure, each wafer was subjected to post-exposure baking on a hotplate at a temperature of 120° C. for 60 seconds and then to paddle development for 60 seconds with an aqueous solution of 2.38% tetramethylammonium hydroxide.

Each of a bright field pattern developed on the organic anti-reflective coating substrate after the development was observed with a scanning electron microscope, and the results of which are shown in Table 2. The term "bright field pattern", as used herein, means a pattern obtained by exposure and development through a reticle comprising an outer frame made of a chromium layer (light-shielding layer) and linear chromium layers (light-shielding layers) formed on a glass surface (light-transmitting portion) extending inside the outer frame. Thus, the bright field pattern is such that, after exposure and development, resist layer surrounding the line and space pattern is removed while resist layer corresponding to the outer frame is left on the outer side of the region from which the resist layer is removed.

Effective Sensitivity (ES): It is expressed as the amount of exposure that the line pattern (light-shielding layer) and the space pattern (light-transmitting layer) become 1:1 after exposure through 0.13 μm line and space pattern mask and development. The smaller the amount is, the higher the sensitivity is.

Resolution: It is expressed as the minimum size of space pattern which gave the space pattern split by the line pattern at the exposure amount of the effective sensitivity.

TABLE 2

| Ex. No. | ES (mJ/cm$^2$) | Resolution (μm) |
| --- | --- | --- |
| Ex. 1 | 36.0 | 0.12 |
| Ex. 2 | 24.5 | 0.12 |
| Comp. Ex. 1 | 39.0 | 0.12 |

Examples 3 to 4 and Comparative Examples 2 to 3

Resin

Resin A1

<Acid Generator>

Acid generator B5:

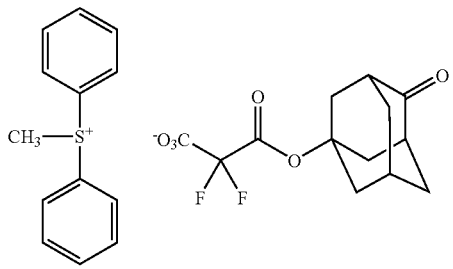

Acid generator B6:

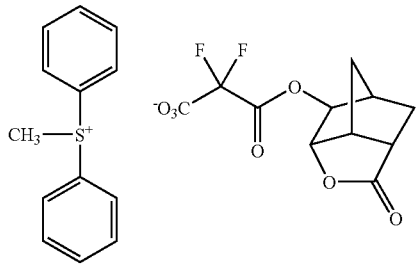

Acid generator C2:

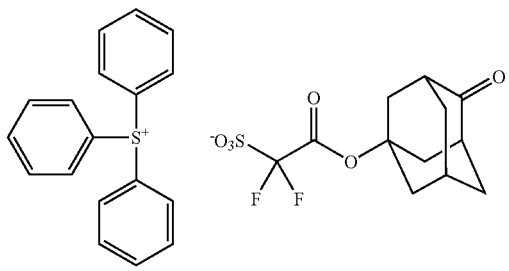

Acid generator C3:

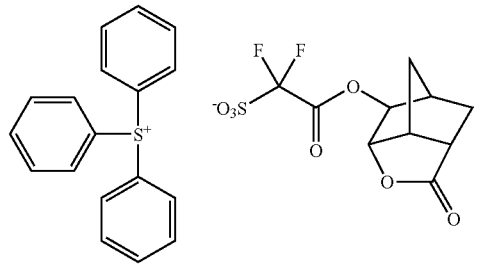

<Quencher>

Quencher Q1: 2,6-diisopropylaniline

<Solvent>

| Solvent Y1: | propylene glycol monomethyl ether acetate | 51.5 parts |
| --- | --- | --- |
| | 2-heptanone | 35.0 parts |
| | γ-butyrolactone | 3.5 parts |

The following components were mixed to give a solution, and the solution was further filtrated through a fluorine resin filter having a pore diameter of 0.2 µm, to prepare resist liquid.

Resin (kind and amount are described in Table 3)
Acid generator (kind and amount are described in Table 3)
Quencher (kind and amount are described in Table 3)
Solvent (kind and amount are described in Table 3)

TABLE 3

| Ex. No. | Resin (kind/amount (part)) | Acid generator (kind/amount (part)) | Quencher (kind/amount (part)) | Solvent |
| --- | --- | --- | --- | --- |
| Ex. 3 | A1/10 | B5/0.23 | Q1/0.0325 | Y1 |
| Ex. 4 | A1/10 | B6/0.23 | Q1/0.0325 | Y1 |
| Comp. Ex. 2 | A1/10 | C2/0.26 | Q1/0.0325 | Y1 |
| Comp. Ex. 3 | A1/10 | C3/0.25 | Q1/0.0325 | Y1 |

Silicon wafers were each coated with "ARC-29A-8", which is an organic anti-reflective coating composition available from Nissan Chemical Industries, Ltd., and then baked under the conditions of 215° C. and 60 seconds, to form a 780 Å-thick organic anti-reflective coating. Each of the resist liquids prepared as above was spin-coated over the anti-reflective coating so that the thickness of the resulting film became 0.25 µm after drying. After application of each of the resist liquids, the silicon wafers thus coated with the respective resist liquids were each prebaked on a direct hotplate at a temperature of 130° C. for 60 seconds. Using an ArF excimer stepper ("FPA5000-AS3" manufactured by CANON INC., NA=0.75, ⅔ Annular), each wafer on which the respective resist film had been thus formed was exposed to a line and space pattern, while changing stepwise the exposure quantity.

After the exposure, each wafer was subjected to post-exposure baking on a hotplate at a temperature of 120° C. for 60 seconds and then to paddle development for 60 seconds with an aqueous solution of 2.38% tetramethylammonium hydroxide.

Each of a dark field pattern developed on the organic anti-reflective coating substrate after the development was observed with a scanning electron microscope, and the results of which are shown in Table 4. The term "dark field pattern", as used herein, means a pattern obtained by exposure and development through a reticle comprising an outer frame made of a chromium layer (light-shielding layer) and linear glass surfaces (light-transmitting portions) formed on chromium layers (light-shielding layers) extending inside the outer frame. Thus, the dark field pattern is such that, after exposure and development, resist layer surrounding the line and space pattern is left.

Effective Sensitivity (ES): It is expressed as the amount of exposure that the line pattern (light-shielding layer) and the space pattern (light-transmitting layer) become 1:1 after exposure through 0.10 µm line and space pattern mask and development. The smaller the amount is, the higher the sensitivity is.

Resolution: It is expressed as the minimum size of space pattern which gave the space pattern split by the line pattern at the exposure amount of the effective sensitivity.

TABLE 4

| Ex. No. | ES (mJ/cm$^2$) | Resolution (µm) |
| --- | --- | --- |
| Ex. 3 | 36.0 | 0.09 |
| Ex. 4 | 35.0 | 0.09 |
| Comp. Ex. 2 | 37.0 | 0.09 |
| Comp. Ex. 3 | 42.0 | 0.09 |

The salt represented by the formula (I) is suitably used for an acid generator capable of providing chemically amplified positive resist compositions giving excellent resist pattern in effective sensitivity, and the present resist composition is especially suitable for ArF excimer laser lithography, KrF excimer laser lithography and ArF immersion lithography.

What is claimed is:

1. A salt represented by the formula (I):

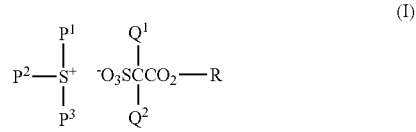

wherein $P^1$, $P^2$ and $P^3$ each independently represent a C1-C30 alkyl group which may be substituted with at least one selected from a hydroxyl group, a C3-C12 cyclic hydrocarbon group and a C1-C12 alkoxy group, or a C3-C30 cyclic hydrocarbon group which may be substituted with at least one selected from a hydroxyl group and a C1-C12 alkoxy group, provided that all of $P^1$, $P^2$ and $P^3$ are not simultaneously phenyl groups which may be substituted, $Q^1$ and $Q^2$ each independently represent a fluorine atom or a C1-C6 perfluoroalkyl group, and R represents a group represented by the formula;

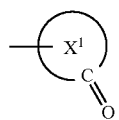

wherein ring $X^1$ represents a C3-C30 monocyclic or polycyclic hydrocarbon group in which one —$CH_2$— group is substituted with —CO—, and at least one hydrogen atom in the monocyclic or polycyclic hydrocarbon group may be substituted with a C1-C6 alkyl group, a C1-C6 alkoxy group, a C1-C4 perfluoroalkyl group, a C1-C6 hydroxyalkyl group, a hydroxyl group or a cyano group;

a group represented by the formula:

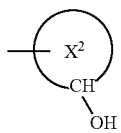

wherein ring $X^2$ represents a C3-C30 monocyclic or polycyclic hydrocarbon group in which a hydrogen atom of one —$CH_2$— group is substituted with a hydroxyl group, and at least one hydrogen atom in the monocyclic or polycyclic hydrocarbon group may be substituted with a C1-C6 alkyl group, a C1-C6 alkoxy group, a C1-C4 perfluoroalkyl group, a C1-C6 hydroxyalkyl group, a hydroxyl group or a cyano group;

a group represented by the formula:

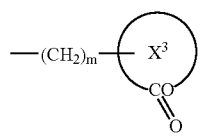

wherein ring $X^3$ represents a C3-C30 monocyclic or polycyclic hydrocarbon group in which one —$CH_2$— group is substituted, with —COO—, and at least one hydrogen atom in the monocyclic or polycyclic hydrocarbon group may be substituted with a C1-C6 alkyl group, a C1-C6 alkoxy group, a C1-C4 perfluoroalkyl group, a C1-C6 hydroxyalkyl group, a hydroxyl group or a cyano group, and m represents an integer of 0 to 12; or a group represented by the formula:

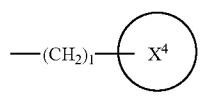

wherein ring $X^4$ represents a C6-C30 polycyclic hydrocarbon group having tricycle or more, and at least one hydrogen atom in the polycyclic hydrocarbon group may be substituted with a C1-C6 alkyl group, a C1-C6 alkoxy group, a C1-C4 perfluoroalkyl group or a cyano group, and l represents an integer of 1 to 12.

2. The salt according to claim 1, wherein $Q^1$ and $Q^2$ each independently represent a fluorine atom or a trifluoromethyl group.

3. The salt according to claim 1, wherein the salt is one represented by the formula (Ib):

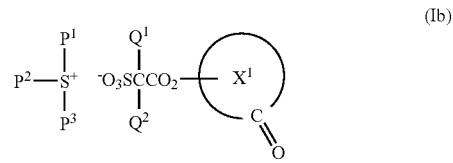

wherein $P^1$, $P^2$, $P^3$, $Q^1$, $Q^2$, and $X^1$ have the same meanings as defined in claim 1.

4. The salt according to claim 3, wherein ring $X^1$ is a C4-C8 oxocycloalkyl group, an oxoadamantyl group or an oxonorbornyl group, and at least one hydrogen atom in each of the groups may be substituted with a C1-C6 alkyl group, a C1-C6 alkoxy group, a C1-C4 perfluoroalkyl group, a C1-C6 hydroxyalkyl group, a hydroxyl group or a cyano group.

5. The salt according to claim 1, wherein the salt is one represented by the formula (Ic):

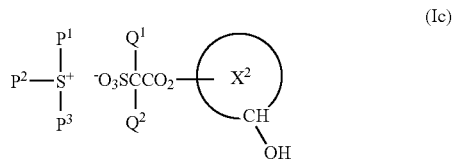

wherein $P^1$, $P^2$, $P^3$, $Q^1$, $Q^2$, and $X^2$ have the same meanings as defined in claim 1.

6. The salt according to claim 5, wherein ring $X^2$ is a C4-C8 hydroxycycloalkyl group, a hydroxyadamantyl group or a hydroxynorbornyl group, and at least one hydrogen atom in each of the groups may be substituted with a C1-C6 alkyl group, a C1-C6 alkoxy group, a C1-C4 perfluoroalkyl group, a C1-C6 hydroxyalkyl group, a hydroxyl group or a cyano group.

7. The salt according to claim 1, wherein the salt is one represented by the formula (Id):

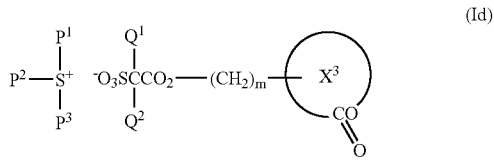

wherein $P^1$, $P^2$, $P^3$, $Q^1$, $Q^2$, $X^3$ and m have the same meanings as defined claim 1.

8. The salt according to claim 7, wherein ring $X^3$ is a monovalent residue of a compound represented by the formula (IIa), (IIb) or (IIc):

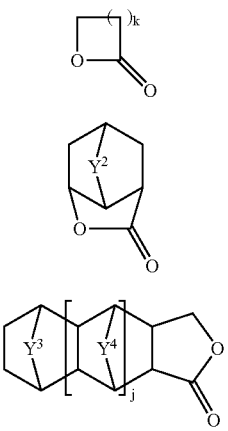

wherein $Y^2$, $Y^3$ and $Y^4$ each independently represent (a) an alkylene group or (b) no bonding and a hydrogen atom in each side, k represents an integer of 1 to 4, j represents an integer of 0 to 2, and at least one hydrogen atom in the formulae (IIIa), (IIIb) and (IIIc) may be substituted with a C1-C6 alkyl group, a C1-C6 alkoxy group, a C1-C4 perfluoroalkyl group, a C1-C6 hydroxyalkyl group, a hydroxyl group or a cyano group.

9. The salt according to claim 1, wherein the salt is one represented by the formula (Ie):

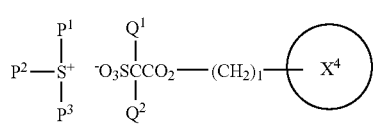

wherein $P^1$, $P^2$, $P^3$, $Q^1$, $Q^2$, $X^4$ and l have the same meanings as defined in claim 1.

10. The salt according to claim 9, wherein ring $X^4$ is a monovalent residue of a compound represented by the formula (IIIa) or (IIIb):

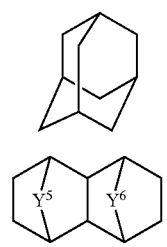

wherein $Y^5$ represents (a) an alkylene group or (b) an oxygen atom, and $Y^6$ represents (a) an alkylene group, (b) an oxygen atom or (c) no bonding and a hydrogen atom in each side, and at least one hydrogen atom in the formulae (IIIa) and (IIIb) may be substituted with a C1-C6 alkyl group, a C1-C6 alkoxy group, a C1-C4 perfluoroalkyl group or a cyano group.

11. The salt according to any one of claims 1-2 and 3-10, wherein at least two selected from $P^1$, $P^2$ and $P^3$ are independently aryl groups which may be substituted with at least one selected from a hydroxyl group and a C1-C12 alkoxy group.

12. The salt according to claim 3, wherein the salt represented by the formula (Ib) is one represented by the formula (IVe) or (IVf);

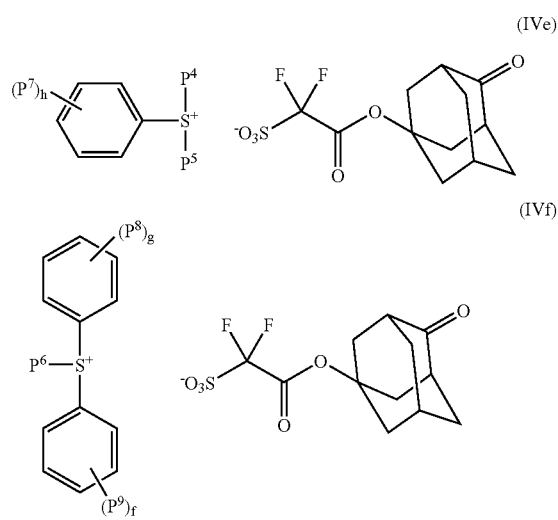

wherein $P^4$ and $P^5$ each independently represent a C1-C20 alkyl group which may be substituted with at least one selected from a hydroxyl group, a C3-C12 cyclic hydrocarbon group and a C1-C12 alkoxy group, or a C3-C30 cyclic hydrocarbon group which may be substituted with at least one selected from a hydroxyl group and a C1-C12 alkoxy group, provided that all of $P^4$ and $P^5$ are not simultaneously phenyl groups which may be substituted, $P^6$ represents a C1-C20 alkyl group which may be substituted with at least one selected from a hydroxyl group, a C3-C12 cyclic hydrocarbon group and a C1-C12 alkoxy group, or a C3-C30 cyclic hydrocarbon group which may be substituted with at least one selected from a hydroxyl group and a C1-C12 alkoxy group, provided that $P^6$ is not a phenyl group which may be substituted, and $P^7$, $P^8$ and $P^9$ each independently represent a hydroxyl group, a C1-C12 alkyl group, a C1-C12 alkoxy group or a C3-C12 cyclic hydrocarbon group, and f, g and h each independently represent an integer of 0 to 5.

13. The salt according to claim 5, wherein the salt represented by the formula (Ic) is one represented by the formula (IVg) or (IVh);

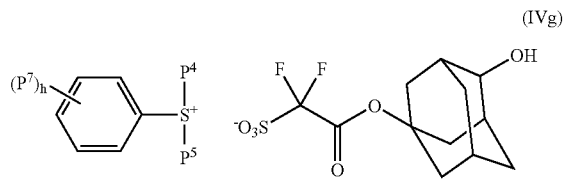

-continued (IVh)

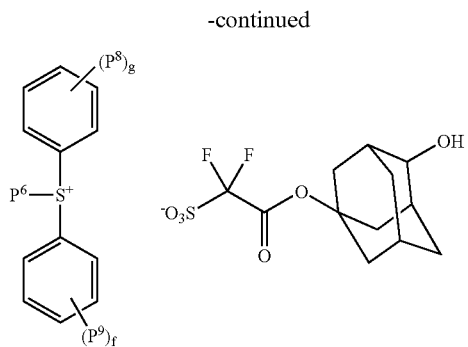

wherein P⁴ and P⁵ each independently represent a C1-C20 alkyl group which may be substituted with at least one selected from a hydroxyl group, a C3-C12 cyclic hydrocarbon group and a C1-C12 alkoxy group, or a C3-C30 cyclic hydrocarbon group which may be substituted with at least one selected from a hydroxyl group and a C1-C12 alkoxy group, provided that all of P⁴ and P⁵ are not simultaneously phenyl groups which may be substituted, P⁶ represents a C1-C20 alkyl group which may be substituted with at least one selected from a hydroxyl group, a C3-C12 cyclic hydrocarbon group and a C1-C12 alkoxy group, or a C3-C30 cyclic hydrocarbon group which may be substituted with at least one selected from a hydroxyl group and a C1-C12 alkoxy group, provided that P⁵ is not a phenyl group which may be substituted, and P⁷, P⁸ and P⁹ each independently represent a hydroxyl group, a C1-C12 alkyl group, a C1-C12 alkoxy group or a C3-C12 cyclic hydrocarbon group, and f, g and h each independently represent an integer of 0 to 5.

14. The salt according to claim 7, wherein the salt represented by the formula (Id) is one represented by the formula (IVi), (IVj), (IVk) or (IVl):

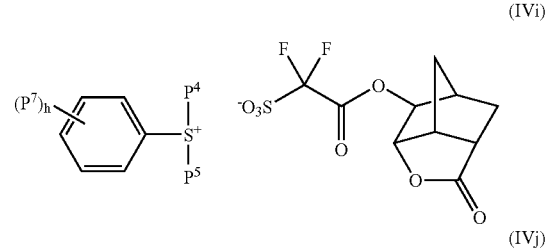

(IVi)

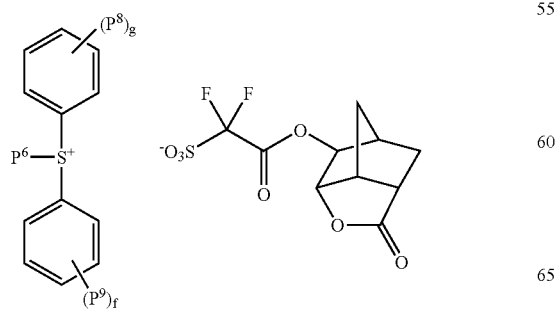

(IVj)

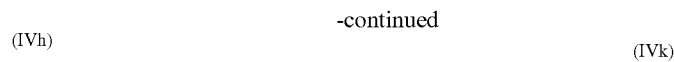

(IVk)

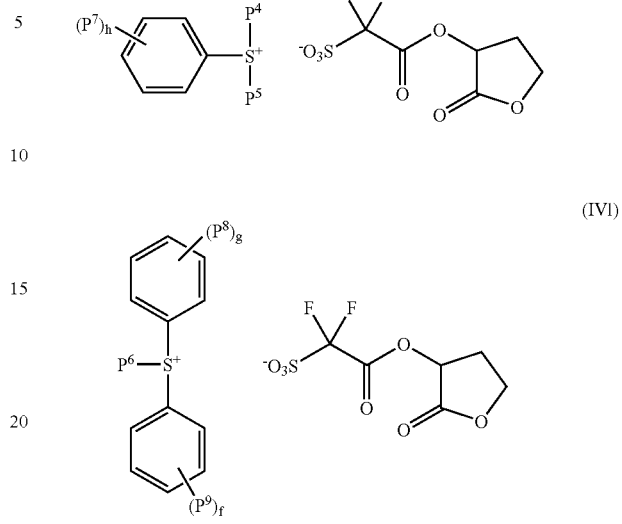

(IVl)

wherein P⁴ and P⁵ each independently represent a C1-C20 alkyl group which may be substituted with at least one selected from a hydroxyl group, a C3-C12 cyclic hydrocarbon group and a C1-C12 alkoxy group, or a C3-C30 cyclic hydrocarbon group which may be substituted with at least one selected from a hydroxyl group and a C1-C12 alkoxy group, provided that all of P⁴ and P⁵ are not simultaneously phenyl groups which may be substituted, P⁶ represents a C1-C20 alkyl group which may be substituted with at least one selected from a hydroxyl group, a C3-C12 cyclic hydrocarbon group and a C1-C12 alkoxy group, or a C3-C30 cyclic hydrocarbon group which may be substituted with at least one selected from a hydroxyl group and a C1-C12 alkoxy group, provided that P⁶ is not a phenyl group which may be substituted, and P⁷, P⁸ and P⁹ each independently represent a hydroxyl group, a C1-C12 alkyl group, a C1-C12 alkoxy group or a C3-C12 cyclic hydrocarbon group, and f, g and h each independently represent an integer of 0 to 5.

15. The salt according to claim 9, wherein the salt represented by the formula (Ie) is one represented by the formula (IVm) or (IVn):

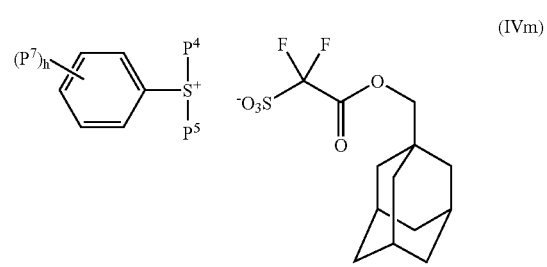

(IVm)

-continued

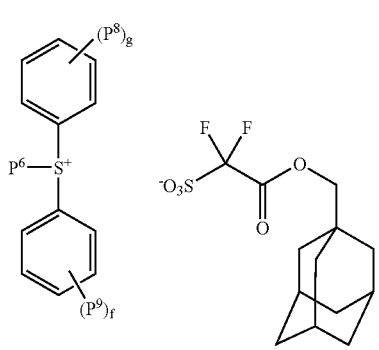
(IVn)

wherein $P^4$ and $P^5$ each independently represent a C1-C20 alkyl group which may be substituted with at least one selected from a hydroxyl group, a C3-C12 cyclic hydrocarbon group and a C1-C12 alkoxy group, or a C3-C30 cyclic hydrocarbon group which may be substituted with at least one selected from a hydroxyl group and a C1-C12 alkoxy group, provided that all of $P^4$ and $P^5$ are not simultaneously phenyl groups which may be substituted, $P^6$ represents a C1-C20 alkyl group which may be substituted with at least one selected from a hydroxyl group, a C3-C12 cyclic hydrocarbon group and a C1-C12 alkoxy group, or a C3-C30 cyclic hydrocarbon group which may be substituted with at least one selected from a hydroxyl group and a C1-C12 alkoxy group, provided that $P^6$ is not a phenyl group which may be substituted, and $P^7$, $P^8$ and $P^9$ each independently represent a hydroxyl group, a C1-C12 alkyl group, a C1-C12 alkoxy group or a C3-C12 cyclic hydrocarbon group, and f, g and h each independently represent an integer of 0 to 5.

16. A chemically amplified positive resist composition comprising a salt represented by the formula (I):

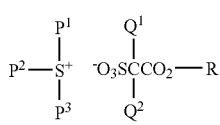
(I)

wherein $P^1$, $P^2$ and $P^3$ each independently represent a C1-C30 alkyl group which may be substituted with at least one selected from a hydroxyl group, a C3-C12 cyclic hydrocarbon group and a C1-C12 alkoxy group, or a C3-C30 cyclic hydrocarbon group which may be substituted with at least one selected from a hydroxyl group and a C1-C12 alkoxy group, provided that all of $P^1$, $P^2$ and $P^3$ are not simultaneously phenyl groups which may be substituted, $Q^1$ and $Q^2$ each independently represent a fluorine atom or a C1-C6 perfluoroalkyl group, and R represents
a group represented by the formula:

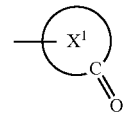

wherein ring $X^1$ represents a C3-C30 monocyclic or polycyclic hydrocarbon group in which one —$CH_2$— group is substituted with —CO—, and at least one hydrogen atom in the monocyclic or polycyclic hydrocarbon group may be substituted with a C1-C6 alkyl group, a C1-C6 alkoxy group, a C1-C4 perfluoroalkyl group, a C1-C6 hydroxyalkyl group, a hydroxyl group or a cyano group;

a group represented by the formula:

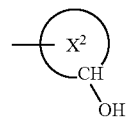

wherein ring $X^2$ represents a C3-C30 monocyclic or polycyclic hydrocarbon group in which a hydrogen atom of one —$CH_2$— group is substituted with a hydroxyl group, and at least one hydrogen atom in the monocyclic or polycyclic hydrocarbon group may be substituted with a C1-C6 alkyl group, a C1-C6 alkoxy group, a C1-C4 perfluoroalkyl group, a C1-C6 hydroxyalkyl group, a hydroxyl group or a cyano group;

a group represented by the formula:

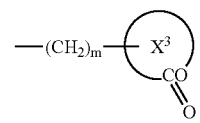

wherein ring X represents a C3-C30 monocyclic or polycyclic hydrocarbon group in which one —$CH_2$— group is substituted with —COO—, and at least one hydrogen atom in the monocyclic or polycyclic hydrocarbon group may be substituted with a C1-C6 alkyl group, a C1-C6 alkoxy group, a C1-C4 perfluoroalkyl group, a C1-C6 hydroxyalkyl group, a hydroxyl group or a cyano group, and m represents an integer of 0 to 12; or a group represented by the formula:

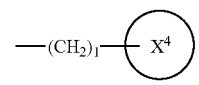

wherein ring $X^4$ represents a C6-C30 polycyclic hydrocarbon group having tricycle or more, and at least one hydrogen atom in the polycyclic hydrocarbon group may be substituted with a C1-C6 alkyl group, a C1-C6 alkoxy group, a C1-C4 perfluoroalkyl group or a cyano group, and l represents an integer of 1 to 12, and a resin which contains a structural unit which has an acid-labile group and which itself is insoluble or poorly soluble in an aqueous alkali solution but becomes soluble in an aqueous alkali solution by the action of an acid.

17. The chemically amplified positive resist composition according to claim 16, wherein $Q^1$ and $Q^2$ each independently represent a fluorine atom or a trifluoromethyl group.

18. The chemically amplified positive resist composition according to claim 16 or 17, wherein the resin contains a structural unit derived from a monomer having a bulky and acid-labile group.

19. The chemically amplified positive resist composition according to claim 18, wherein the bulky and acid-labile group is a 2-alkyl-2-adamantyl ester group or a 1-(1-adamantyl)-1-alkylalkyl ester group.

20. The chemically amplified positive resist composition according to claim 18, wherein the monomer having a bulky and acid-labile group is 2-alkyl-2-adamantyl acrylate, 2-alkyl-2-adamantyl methacrylate, 1-(1-adamantyl)-1-alkylalkyl acrylate, 1-(1-adamantyl)-1-alkylalkyl methacrylate, 2-alkyl-2-adamantyl 5-norbornene-2-carboxylate, 1-(1-adamantyl)-1-alkylalkyl 5-norbornene-2-carboxylate, 2-alkyl-2-adamantyl α-chloroacrylate or 1-(1-adamantyl)-1-alkylalkyl α-chloroacrylate.

21. The chemically amplified positive resist composition according to claim 16 or 17, wherein the chemically amplified positive resist composition further comprises a basic compound.

* * * * *